US006884623B1

(12) United States Patent
Lomonossoff et al.

(10) Patent No.: US 6,884,623 B1
(45) Date of Patent: Apr. 26, 2005

(54) MODIFIED PLANT VIRUSES AS VECTORS OF HETEROLOGOUS PEPTIDES

(75) Inventors: George P. Lomonossoff, Norfolk (GB); John E. Johnson, San Diego, CA (US); Mary Bendig, Villanova, PA (US); Tim Jones, Cambridge (GB); Marian Longstaff, Cambridge (GB)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/304,967

(22) Filed: May 5, 1999

Related U.S. Application Data

(63) Continuation-in-part of application No. 08/612,858, filed on Jun. 5, 1996, now Pat. No. 5,958,422, and a continuation-in-part of application No. 08/471,048, filed on Jun. 6, 1995, now Pat. No. 5,874,087, and a continuation-in-part of application No. 08/137,032, filed as application No. PCT/GB92/00589 on Apr. 2, 1992, now Pat. No. 6,110,466.

(30) Foreign Application Priority Data

Apr. 19, 1991 (GB) .............................................. 9108386

(51) Int. Cl.$^7$ .......................... C12N 5/04; C12N 15/83; C12N 15/63; C12N 5/10

(52) U.S. Cl. .............................. 435/468; 435/5; 435/6; 435/235.1; 435/239; 435/410; 435/472; 435/419; 536/23.1; 536/23.6; 536/23.72

(58) Field of Search ................................ 435/5, 6, 455, 435/456, 235.1, 239, 410, 419, 468, 472, 320.1; 536/23.1, 23.6, 23.72

(56) References Cited

U.S. PATENT DOCUMENTS

| 4,407,956 | A | | 10/1983 | Howell |
|---|---|---|---|---|
| 4,593,002 | A | | 6/1986 | Dulbecco |
| 4,722,840 | A | | 2/1988 | Valenzuela et al. |
| 5,316,931 | A | * | 5/1994 | Donson et al. ............. 435/455 |
| 5,596,132 | A | * | 1/1997 | Zaitlin et al. ............... 800/205 |
| 5,874,087 | A | * | 2/1999 | Lomonossoff et al. ... 424/199.1 |
| 5,958,422 | A | * | 9/1999 | Lomonossoff et al. ... 424/199.1 |

FOREIGN PATENT DOCUMENTS

| EP | 067 553 A3 | 12/1982 |
|---|---|---|
| EP | 0174759 | 3/1986 |
| EP | 194 809 A1 | 9/1986 |
| EP | 221 044 A1 | 5/1987 |
| WO | WO87/06261 | 10/1987 |
| WO | WO89/08145 | 4/1989 |
| WO | WO90/00611 | 1/1990 |
| WO | WO91/13994 | 9/1991 |
| WO | WO91/15587 | 10/1991 |
| WO | WO92/18618 | 10/1992 |
| WO | WO93/03161 | 2/1993 |
| WO | WO95/21248 | 8/1995 |

OTHER PUBLICATIONS

Chapman et al. Potato virus X as a vector for gene expression in plants. The Plant J. vol. 2(4):549–557, 1992.*
Chan, et al. "Capsid Structure and RNA packaging in comoviruses," Seminars in Virology, vol. 1, 1990: pp 453–466.
Abstract W47–007–Submitted to 8$^{th}$ International Congress of Virology in Berlin in 1990.
Haynes, et al. "Development of a Genetically–engineered, candidate polio vaccine employing the self–assembling properties of the tobacco mosaic virus coat protein." Biotechnology, vol. 4, pp. 637–641, 1986.
Evans, et al. "An engineered polio virus chimaera elicits broadly reactive HIV–1 neutralizing antibodies." Nature, vol. 339, pp. 385–388, 1989.
Koff, et al. "Progress and chaooenges toward an AIDS vaccine: Brother can you spare a paradigm?" Journal of Clinical Immunology, vol. 16(3) pp. 127–133, 1996.
Usha, et al. "Expression of an Animal Virus Antigenic Site on the Surface of a Plant Virus Particle," Virology, vol. 197, (1993) pp. 366–374.
Kennedy, et al. "Antiserum to a Synthetic Peptide Recognizes the HTLV–III Envelope Glycoprotein," Science, vol. 231, Mar. 28, 1986, pp. 1556–1559.
Chant and Hoof, "Cowpea Mosaic Virus," CMI/AAB Descriptions of Plant Virus, Aug. 1978, No. 197 (No. 47 Revised.).
Dessens and Lomonossoff, "Cauliflower Mosaic virus 35S promoter–controlled DNA copies of cowpea mosaic virus RNAs are infectious on plants," Journal of general virology (1993), vol. 74, pp. 889–892.
FEBS Letters, vol. 269, No. 1, Aug. 1990, Amsterdam NL, pp. 73–76, Takamatsu, et al. "Production of Enkephalin in Tobacco Protoplasts Using Tobacco Mosaic Virus RNA Vector."
BIOTECHNOLOGY, vol. 11, No. 8–93, New York US, pp. 930–932, Hamamoto, et al. "A New Tobacco Mosaic Virus Vector and its use for the systemic production of Angiotensin–I–Coverting Enzyme Inhibitor in Transgenic Tobacco and Tomato.", 1983.
VIROLOGY, vol. 197, 1993, pp. 366–374, Usha et al. "Expression of Animal Virus Antigenic Site on the surface of a plant viral particle," p. 367 "Construction of pMT7–FMCV–1 and pMT7–FMDV–II" and "In Vitro Transcription Reactions."
VIROLOGY, vol. 202, Aug. 1, 1994, pp. 949–955. Porta, et al. "Development of Cowpea Mosaic Virus as a High–Yielding System for the Presentation of Foreign Antigens."

(Continued)

Primary Examiner—David Guzo

(57) ABSTRACT

The invention relates to assembled particles of a plant virus containing a foreign peptide insert in the coat protein of the virus. The site of the insert is preferably free from direct sequence repeats flanking the insert. The invention relates to a method of production of the particles and their use, in particular in vaccines.

9 Claims, 24 Drawing Sheets

OTHER PUBLICATIONS

Aids Research and Human Retroviruses, vol. 11, No. 3, Mar. 1995, pp. 327–224, McLain, et al. "Human Immunodeficiency Virus Type–1 Neutralizing Antibodies Raised to a Glycoprotein 41 peptide Expressed on the surface of a Plant Virus."

Proceedings of the National Academy of Sciences of USA, vol. 88, Aug. 1991, pp. 7204–7208, Donson, et al. "Systemic Expression of a Bacterial Gene by a Tobacco Mosaic Virus–Based Vector."

Ahlquist, et al. "cDNA Cloning and In Vitro Transcription of the Complete Brome Mosaic Virus Genome," *Molecular and Cellular Biology*, vol. 4, No. 12, Dec. 1984, pp. 2876–2882.

Biggin, M.D., et al. "Buffer Gradient Gels and 35S label as an aid to rapid DNA sequency determination," *Proc. Natl. Acad. Sci.*, vol. 80, pp. 3963–3965, Jul. 1983.

Birnboim, et al. "A rapid alkaline extraction procedure for screening recombinant plasmid DNA," *Nucleic Acids Research*, vol. 7, No. 6, 1979, pp. 1513–1523.

Chanh, et al. "Induction of anti–HIV neutralizing antibodies by synthetic peptides," *The EMBO Journal*, vo. 5, No. 11, pp. 3065–3071, 1986.

Dalgleish, et al. "Neutralization of Diverse HIV–1 Strains by Monoclonal Antibodies Raised against a gp41 Synthetic peptide."*Virology*, vol. 165, pp. 209–215, 1988.

De Varennes, et al. "Independent replication of cowpea mosaic virus bottom component RNA: in vivo Instability of the viral RNAs," *Virology*, vol. 144, p. 495–501, 1985.

Dessens, et al. "Mutational Analysis of the putative catalytic triad of the cowpea mosaic virus 24K Protease," *Virology*, vol. 184, pp. 738–746, 1991.

Feinberg, et al. "A Technique for Radiolabeling DNA restriction Endonuclease Fragments to High Specific Activity," *Analytic Biochemistry.* vol. 132, pp. 6–13, 1983.

Goldbach, et al. "Independent Replication and expression of B–component RNA of cowpea mosaic virus,"*Nature,*vol. 286, pp. 297–300, 1980.

Holness, C.L.L. "Isolation and characterisation of Mutants of cowpea mosaic virus," Doctoral Thesis submitted to the University of Warwick, 9/89, 1989.

Kennedy, et al. "Antiserum to a synthetic peptide recogmizes the HTLV–III Envelope Glycoprotein,"*Science*, vol. 231, pp. 1556–1559, 1986.

Holness, et al. "Identification of the Initiation of Codons for Translation of Cowpea Mosaic Virus Middle Component RNA using Site–Directed Mutagenesis of an Infectious cDNA Clone," *Virology*, vol. 172, pp. 311–320, 1989.

Kunkel, "Rapid and efficient site–specific mutagenesis without phenotypic selection," Proc. Natl. Acad. Sci, vol. 82, pp. 488–492, Jan. 1985.

Laemmli, "Cleavage of Structural Proteins during the assembly of the Head Bacteriophage T4," *Nature*, vol. 227, pp. 680–685, 1970.

Lehrach, et al. "RNA Molecular Weight Determination by Gel Electrophoresis under Denaturing Conditions, a critical reexamination," *Biochemistry*, vol. 16, No. 21, pp. 4743–4751, 1977.

Lomonossoff, et al. "The Nucleotide Sequence of cowpea mosaic virus RNAs," *The EMBO Jouranl* ,vol. 2, No. 12, pp. 2253–2258, 1983.

Lomonossoff, et al. "The location of the fist AUG codons in cowpea mosaic virus RNAs," *Nucleic Acids Research*, vol. 10, No. 16, pp. 4861–4872, 1982.

Maniatis, et al. "Molecular Cloning, a Laboratory Manual," Cold Spring Harbor Laboratory, 1982.

Pelham, et al. "An Efficient mRNA–Dependent Translation System from Reticulocyte Lysates," Eur. J. Biochem, vol. 67, pp. 247–256, 1982.

Sanger, et al. "Cloning in Single–Stranded Bacteriophage as an aid to rapid DNA sequencing," J. Mol. Biol., vol. 143, pp. 161–178, 1980.

Shanks, et al. "The primary structure of Red Clover Mottle Virus Middle Component RNA," *Virology,*vol. 155, pp. 697–706, 1986.

Van Wezenbeck, et al. "Primary Structure and gene organization of the middle–component RNA of cowpea mosaic virus," The EMBO Journal, vol. 2, No. 6, pp. 941–946, 1983.

Zeigler–Graff, et al. "Biologically Active Transcripts of Beet Necrotic Yellow Vein Virus RNA–3 and RNA–4," J. gen. Virol. vol. 69, pp. 2347–2357, 1988.

"Production of Enkephalin in Tobacco Protoplasts using Tobacco Mosaic Virus RNA Vector," Takamatsu, et al. vol. 269, No. 1, pp. 73–76, Aug. 1990.

Sherry, et al. "Use of Monoclonal Antibodies to Identify Four Neutralization Immunogens on a Common Cold Picornavirus, Human Rhinovirus 14," *Journal of Virology,*Jan. 1986, pp. 246–257.

* cited by examiner

```
            1         5              10             15    βB     20              25
            G  P  V  C  A  E  A  S  D  V  Y  S  P  C  M  I  A  S  T  P  P  A  P  F  S
         GGACCTGTTTGTGCTGAAGCCTCAGATGTGTATAGCCCATGTATGATAGCTAGCACTCCTCCTGCTCCATTTTCA
            2670                        2700       NheI            2730
```

```
               βC
            30         35           40
         D  V  T  A  V  T  F  D  L  I  N  G  K  I  T
       GACGTTACAGCAGTAACTTTTGACTTAATCAACGGCAAAATAACT
                        2760
```

FIG. 1

```
    S  T  Y  S  R  N  A  V  P  N  L  R  G  D  L  Q  V  L  A  Q  K  V  A  R  T  L  P
CTAGCACTTATAGTAGAAATGCTGTTCCTAATTTGAGAGGAGATCTTCAAGTTTTGGCTCAAAAGGTTGCTCGGACTCTTC
GTGAATATCATCTTTACGACAAGGATTAAACTCTCCTCTAGAAGTTCAAAACCGAGTTTTCCAACGAGCCTGAGAAGGATC
                                     BglII
```

FIG. 2A

```
   1             5                 10                15
   G  P  V  C  A  E  A  S  D  V  Y  S  P  C  M  I  A  S  T  Y  S  R  N  A  V  P  N
GGACCTGTTTGTGCTGAAGCCTCAGATGTGTATAGCCCATGTATGATAGCTAGCACTTATAGTAGAAATGCTGTTCCTAAT
                                  2670                    2700
                                                          NheI

L  R  G  D  L  Q  V  L  A  Q  K  V  A  R  T  L  P  S  T  P  P  A  P  F  S
TTGAGAGGAGATCTTCAAGTTTTGGCTCAAAAGGTTGCTCGGACTCTTCCTAGCACTCCTCCTGCTCCATTTTCA
           BglII                                           xNheI         2730
```

FIG. 2B

```
      βB
11  ←――――――→  136
Y  S  P  C  M  I  A  S  T  Y  S  R  N  A  V  P  N  L  R  G  D  L  Q  V  L  A
TATAGCCCATGTATGATAGCTAGCACTTATAGTAGAAATGCTGTTCCTAATTGAGAGGAGATCTTCAAGTTTTGGCT
ATATCGGGTACATACTATCGATCGTGAATATCATCTTTACGACAAGGATTAAACTCTCCTCTAGAAGTTCAAAACCGA
                        NheI                                    BgIII

βC
                                   ←――――――→
                                      30
Q  K  V  A  R  T  L  P  S  T  P  P  A  P  F  S  D  V  T  A  V  T  F  D  L  I
CAAAAGGTTGCTCGGACTCTTCCTAGCACTCCTCCTGCTCCATTTTCAGACGTTACAGCAGTAACTTTTGACTTAATC
GTTTTCCAACGAGCCTGAGAAGGATCGTGAGGAGGACGAGGTAAAAGTCTGCAATGTCGTCATTGAAAACTGAATTAG
                  xNheI
```

FIG. 3

```
    S  T  D  R  P  E  G  I  E  E  G  G  E  R  D  R  D  R  S  D
CTAGCACTGACCGCCCCTGAGGGCATCGAGGAAGAGGGGCGGTGAGCGCGATCGTGATCGTTCGGACGT
GTGACTGGCGGGACTCCCGTAGCTCCTTCTCCCGCCACTCGCCGCTAGCACTAGCCAAGCC
                                                    Pvul
```

FIG. 5A

```
 1                5                10               15
 G  P  V  C  A  E  A  S  D  V  Y  S  P  C  M  I  A  S  T  D  R  P  E  G  I  E
GGACCTGTTTGTGCTGAAGCCCTGAGATCGTGTATAGCCCCATGTATGATAGCTAGCACTGACCGCCCCTGAGGGCATCGAG
            2670                        2700                    NheI 30              35
 E  E  G  G  E  R  D  R  D  R  S  D  V  T  A  V  T  F  D  L  I
GAAGAGGGGCGGTGAGCGCGATCGTGATCGTTCGGACGTCACAGCAGTAACTTTTGACTTAATC
                Pvul                AatII              2760
```

FIG. 5B

```
    S  T  P  A  T  G  I  D  N  H  R  E  A  K  L  D
CTAGCACTCCTGCTACTGGAATCGATAATCATAGAGAAGCTAAATTGGACGT
GTGAGGACGATGACCTTAGCTATTAGTATCTCTTCGATTTAACC
                         ClaI
```

FIG. 6A

```
    1                   5                   10                  15
    G  P  V  C  A  E  A  S  D  V  Y  S  P  C  M  I  A  S  T  P  A  T  G  I  D  N
GGACCCTGTTTGTGCTGAAGCCTCAGATGTGTATAGCCCATGTATGATAGCTAGCACTCCTGCTACTGGAATCGATAAT
2670                      2700                                          ClaI
                                                    NheI
                20                  25                  30                  35
H  R  E  A  K  L  D  V  T  A  V  T  F  D  L  I
CATAGAGAAGCTAAATTGGACGTCACAGCAGTAACTTTTGACTTAATC
                      AatII                2760
```

FIG. 6B

```
            ←――― βB ―――→
     11                        140
     Y  S  P  C  M  I  A  S  T  V  P  N  L  R  G  D  L  Q  V  L  A
     TATAGCCCATGTATGATAGCTAGCACTGTTCCTAATTTGAGAGGAGATCTTCAAGTTTTGGCT
     ATATCGGGTACATACTATCGATCGTGACAAGGATTAAACTCTCCTCTAGAAGTTCAAAACCGA
                      NheI                        BglII

←―― βC ――→
                     160      30
     Q  K  V  A  R  T  L  P  D  V  T  A  V  T  F  D  L  I
     CAAAAGGTTGCTCGGACTCTTCCTGACGTCACAGCAGTAACTTTTGACTTAATC
     GTTTTCCAACGAGCCTGAGAAGGACTGCAGTGTCGTCATTGAAAACTGAATTAG
                          AatII
```

FIG. 7

```
  20          P  P  A
S  T  P  P  A
CTAGCACTCCTCCTGCT
GTCAGGAGGACGA
```

```
                                    25
                                 P  P  S  D
                                 CCATTTTCAGACGT
                                 GGTAAAAGTC
```

```
141
V  P  N  L  R  G  D  L  Q  V  L  A  Q  K  V  A  R  T  L
GTTCCTAATTTGAGAGGAGATCTTCAAGTTTTGGCTCAAAAGGTTGCTCGGACTCTT
CAAGGATTAAACTCTCCTCTAGAAGTTCAAAACCGAGTTTTCCAACGAGCCTGAGAA

FMDV-V
```

SEQUENCE OF SBMV COAT PROTEIN SPANNING THE POTENTIAL INSERTION SITE WITH
INTRODUCED BASE CHANGES AND NEW RESTRICTION SITES:(SEQUENCE STARTS AT nt 3955)

```
        M  E  G  G  S  S  K  T  A  V  N  T  G
        ATGGAAGGAGGATCATCTAAGACTGCTGTGAACACTGGG
                   ↓                  ↓
                 GGATCC             GTTAAC
                 BamH I             Hpa I
```

FIG. 11A

SERIES OF SEQUENCES TO BE INSERTED BETWEEN THE RESTRICTION SITES TO INSERT
THE MUC1(16) EPITOPE AT VARIOUS LOCATIONS

```
     G  V  T  S  A  P  D  T  R  P  A  P  G  S  T  A
     GGTGTTACTTCTGCTCCTGATACTAGACCTGCTCCTGGTTCTACTGCT
     CCACAATGAAGACGACCACTATGATCTGGACGAGGACCAAGATGACGA
     ←                          ↓     ↓                →

GATCC              TCTAAGACTGCTGTT
                  G                  AGATTCTGACGACAA

GATCCTCT           AAGACTGCTGTT
                  GAGA               TTCTGACGACAA

GATCCTCTAAG        ACTGCTGTT
                  GAGATTC            TGACGACAA

GATCCTCTAAGACT     GCTGTT
                  GAGATTCTGA         CGACAA

GATCCTCTAAGACTGCT  GTT
                  GAGATTCTGACGA      CAA
```

FIG. 11B

```
LTSV : NI---YAPARLTIAA-ANSSINIASVGTLYATYEVEL

SBMV : NIGNILVPARLVIAMEGGSSKTAVNTGRLYASYTIRL

SMV  : NIATDLVPARLVIALLDGSSSTAVAAGRIYASYTIQM

#######======#############
          βH    loop      βI
```

FIG. 12

SEQUENCE OF LTSV COAT PROTEIN SPANNING THE POTENTIAL INSERTION SITE WITH
INTRODUCED BASE CHANGES AND NEW RESTRICTION SITES: (SEQUENCE STARTS AT nt 3954)

```
    I  A  A  A  N  S  S  I  N  I  A  S  V  G  T  L  Y
    ATAGCCGCAGCTAACAGCTCCATAAACATAGCTAGTGTGGGTACTCTTTAT
            ↓                                ↓
          CTGCAG                           GGTACC
          Pst I                            Kpn I
```

FIG. 13A

SERIES OF SEQUENCES TO BE INSERTED BETWEEN THE RESTRICTION SITES TO INSERT
THE MUC1(16) EPITOPE AT VARIOUS LOCATIONS

```
       G  V  T  S  A  P  D  T  R  P  A  P  G  S  T  A
       GGTGTTACTTCTGCTCCTGATACTAGACCTGCTCCTGGTTCTACTGCT
       CCACAATGAAGACGACCACTATGATCTGGACGAGGACCAAGATGACGA
    ↙                                                    ↘
    ↓                                                    ↓
```

| | |
|---|---|
| GCTAACAGC | TCCATAAACATAGCTAGTGTGGGTAC |
| ACGTCGATTGTCG | AGGTATTTGTATCGATCACACC |
| GCTAACAGCTCC | ATAAACATAGCTAGTGTGGGTAC |
| ACGTCGATTGTCGAGG | TATTTGTATCGATCACACC |
| GCTAACAGCTCCATA | AACATAGCTAGTGTGGGTAC |
| ACGTCGATTGTCGAGGTAT | TTGTATCGATCACACC |
| GCTAACAGCTCCATAAAC | ATAGCTAGTGTGGGTAC |
| ACGTCGATTGTCGAGGTATTTG | TATCGATCACACC |
| GCTAACAGCTCCATAAACATA | GCTAGTGTGGGTAC |
| ACGTCGATTGTCGAGGTATTTGTAT | CGATCACACC |
| GCTAACAGCTCCATAAACATAGCT | AGTGTGGGTAC |
| ACGTCGATTGTCGAGGTATTTGTATCGA | TCACACC |

FIG. 13B

```
LIPMAN-PEARSON PROTEIN ALIGNMENT
KTUPLE: 2; GAP PENALTY: 4; GAP LENGTH PENALTY: 12
SEQ1(1>389)   SEQ2(1>340)    SIMILARITY    GAP       GAP      CONSENSUS
tbsvtbs.PRO   rcnmvdia.PRO     INDEX      NUMBER    LENGTH     LENGTH
(64>387)      (8>338)          26.9          4         7          331
```

```
              ↙70       ↙80       ↙90       ↙100      ↙110      ↙120
       KKQQMINHVGGTGGAIMAPVAVTRQLVGSKPKFTGRTSGSVTVTHREYLSQVNNSTGFQV
       K.:Q. :. . T .: :  .VA:. . .         . ...: .: H :: V .S. .:.
       KSKQRSQPRNRTPNTSVKTVAIPFAKTQIIKTVNPPPKPARGILHTQLVMSVVGSVQMRT
              ↖10       ↖20       ↖30       ↖40       ↖50       ↖60

↙130      ↙140      ↙150      ↙160      ↙170      ↙180
       NGGIVGNLLQLNPLNGTLFSWLPAIASNFDQYTFNSVVLHYVPLCSTTEVGRVAIYFDKD
       N.G   .:  ::LNP N :LF: L:   A:N:D Y ::.:.L:YVPL :. : GRVA: .D D
       NNGKSNQRFRLNPSNPALFPTLAYEAANYDMYRLKKLTLRYVPLVTVQNSGRVAMIWDPD
              ↖70       ↖80       ↖90       ↖100      ↖110      ↖120

↙190      ↙200      ↙210      ↙220      ↙230      ↙240
       SEDPEPADRVELANYSVLKETAPWAEAMLRVPTDKIKRFCDDSSTSDHKLIDLGQLGIAT
       S:D:..P...R E::.YS   .TA ... L :P:D: RF .D::T D:KL:D:GQL :.T
       SQDSAPQSRQEISAYSRSVSTAVYEKCSLTIPADNQWRFVADNTTVDRKLVDFGQLLFVT
              ↖130      ↖140      ↖150      ↖160      ↖170      ↖180

↙250      ↙260      ↙270      ↙280      ↙290      ↙300
       YGGAGTNAVGDIFISYSVTLYFPQPTNTLLSTRRLDLAGALVTASGPGYLLVSR---TAT
       .:G::.. ..GDIF:...V.:  PQPT.:::  .  :DL:G:L.: .GP:YL: :    T::
       HSGSDGIETGDIFLDCEVEFKGPQPTASIVQKTVIDLGGTLTSFEGPSYLMPPDAFITSS
              ↖190      ↖200      ↖210      ↖220      ↖230      ↖240

↙310      ↙320      ↙330      ↙340      ↙350
       VLTMTFRATGTFVISGTYRCLTATTLGLAG--GVNVNSITVVDNIG-TDSAFFINCTVSN
       :.:     .:GT::::  .   C T:.::.:::G  .:  :: :.  ::   ...S  F.:...V :
       SFGLFVDVAGTYLLTLVVTCSTTGSVTVGGNSTLVGDGRAAYGSSNYIASIVFTSSGVLS
              ↖250      ↖260      ↖270      ↖280      ↖290      ↖300

↙360      ↙370      ↙380
       LPSVVTFT-STGITSATVHCVRATRQNDVSL
       .: V F: S:G::.. :: R .: N. L
       TTPSVQFSGSSGVSRVQMNICRCKQGNTFIL
              ↖310      ↖320      ↖330
```

FIG. 14

```
                        220       230       240
         AA      |ASIVQKYVIDLGGTLTSFEGPSYLMPP
         PHD sec |  HHHHHEEEE    EEEE     EEEEE
         Rel sec |14543224452551562558648762 4
detail :
         prH sec |4666553211111000000000000 00
         prE sec |1011234566322467522126887 53
         prL sec |4222211122466422377873112 46
subset : SUB sec |..H......E.LL.EE.LLLL.EEE..
```

```
ABBREVIATIONS:
    AA: AMINO ACID SEQUENCE
    H: HELIX
    E: EXTENDED (SHEET)
    BLANK: OTHER (LOOP)
    PHD: PROFILE NETWORK PREDICTION HEIDELBERG
    Rel: RELIABILITY INDEX OF PREDICTION (0-9)
    prH: PROBABILITY FOR ASSIGNING HELIX
    prE: PROBABILITY FOR ASSIGNING STRAND
    prL: PROBABILITY FOR ASSIGNING LOOP
    SUB: A SUBSET OF THE PREDICTION, FOR ALL RESIDUES
         WITH AN AVERAGE EXPECTED ACCURACY OF >82%
```

FIG. 16

SEQUENCE OF RCNMV COAT PROTEIN SPANNING THE POTENTIAL INSERTION SITE WITH
INTRODUCED BASE CHANGES AND NEW RESTRICTION SITES:(SEQUENCE STARTS AT nt 3070)

```
         S  I  V  Q  K  T  V  I  D  L  G  G  T  L  T  S  F
        AGCATCGTACAGAAAACTGTAATTGATCTCGGTGGGACACTCACTTCTTTC
              ↓  ↓                          ↓     ↓

GTGCAC                         GTTAAC
            Apal I                          Hpal
```

FIG. 17A

SERIES OF SEQUENCES TO BE INSERTED BETWEEN THE RESTRICTION SITES TO INSERT
THE MUC1(16) EPITOPE AT VARIOUS LOCATIONS

```
       G  V  T  S  A  P  D  T  R  P  A  P  G  S  T  A
      GGTGTTACTTCTGCTCCTGATACTAGACCTGCTCCTGGTTCTACTGCT
      CCACAATGAAGACGACCACTATGATCTGGACGAGGACCAAGATGACGA
```

| | |
|---|---|
| GAAAACTGTA | ATTGATCTCGGTGGGACGTT |
| ACGTCTTTTGACAT | TAACTAGAGCCACCCTGCAA |
| GAAAACTGTAATT | GATCTCGGTGGGACGTT |
| ACGTCTTTTGACATTAA | CTAGAGCCACCCTGCAA |
| GAAAACTGTAATTGAT | CTCGGTGGGACGTT |
| ACGTCTTTTGACATTAACTA | GAGCCACCCTGCAA |
| GAAAACTGTAATTGATCTC | GGTGGGACGTT |
| ACGTCTTTTGACATTAACTAGAG | CCACCCTGCAA |
| GAAAACTGTAATTGATCTCGGT | GGGACGTT |
| ACGTCTTTTGACATTAACTAGAGCCA | CCCTGCAA |
| GAAAACTGTAATTGATCTCGGTGGG | ACGTT |
| ACGTCTTTTGACATTAACTAGAGCCACCC | TGCAA |

FIG. 17B

NUCLEOTIDE AND AMINO-ACID SEQUENCE OF THE C-TERMINAL REGION OF THE COAT PROTEIN OF TRV:

```
    S  T  P  A  S  G  G  S  G  A  T  P  P  P  A  S  G  G  A  V  R  P  N  P  *
1125CGTCGACTCCGGCCTCGGGGGGAAGTGGTGCAACACCACCTCCTGCGAGTGGGGGTGCTGTGCGTCCTAATCCTTGATGTCGTCAAATCAAACCTTTAAGGGACCTT1230
    ↑                                                                                                   ↑
   Sal I                                                                                              PpuM I
```

FIG. 18A

SERIES OF SEQUENCES TO BE INSERTED BETWEEN THE Sal I AND PpuM I RESTRICTION SITES TO CREATE C-TERMINAL DELETIONS:

```
 S  T  P  A  S  G  G  S  G  A  T  P  P  P  A  S  G  G  A  *
TCGACTCCGGCCTCGGGGGGAAGTGGTGCAACACCACCTCCTGCGAGTGGGGGTGCTTGATGTCGTCAAATCAAACCTTTAAGG
    GAGGCCGGAGCCCCCCTTCACCACGTTGTGGTGGAGGACGCTCACCCCCACGAACTACAGCAGTTTAGTTTGGAAATTCCCTG

S  T  P  A  S  G  G  S  G  A  T  P  P  P  *
TCGACTCCGGCCTCGGGGGGAAGTGGTGCAACACCACCTCCTTGATGTCGTCAAATCAAACCTTTAAGG
    GAGGCCGGAGCCCCCCTTCACCACGTTGTGGTGGAGGAACTACAGCAGTTTAGTTTGGAAATTCCCTG

S  T  P  A  S  G  G  S  G  *
TCGACTCCGGCCTCGGGGGGAAGTGGTTGATGTCGTCAAATCAAACCTTTAAGG
    GAGGCCGGAGCCCCCCTTCACCAACTACAGCAGTTTAGTTTGGAAATTCCCTG

S  T  P  A  *
TCGACTCCGGCCTGATGTCGTCAAATCAAACCTTTAAGG
    GAGGCCGGACTACAGCAGTTTAGTTTGGAAATTCCCTG

S  T  *
TCGACTTGATGTCGTCAAATCAAACCTTTAAGG
    GAACTACAGCAGTTTAGTTTGGAAATTCCCTG
```

FIG. 18B

MODIFIED PLANT VIRUSES AS VECTORS OF HETEROLOGOUS PEPTIDES

In accordance with the provisions of 35 U.S.C. 120, this application claims the priority and is a continuation-in-part of U.S. patent application Ser. Nos. 08/471,048, filed Jun. 6th, 1995 now U.S. Pat. No. 5,874,087; 08/612,858, filed Jun. 5th, 1996 now U.S. Pat. No. 5,958,422; 08/137,032, filed Dec. 15th, 1993 now U.S. Pat. No. 6,110,466, which is a 371 of PCT/GB92/00589, filed Apr. 2nd, 1992, which claims benefit of the priority under 35 U.S.C. 119 of: Great Britain Patent Application No. 91 08386.5, filed Apr. 16, 1991.

This invention relates to the use of plant viruses as carriers (vectors) for the production or presentation of foreign peptides. More particularly, the invention relates to the genetic manipulation of viral nucleic acid by incorporation of foreign nucleic acid sequences which are expressed as peptides in the virus particle (virion).

Our patent application WO 92/18618 (which is incorporated herein by reference) describes the utilisation of plant viruses as vector systems for the expression of foreign nucleotide sequences, i.e. nucleotide sequences (RNA or DNA) which are not present in plant viruses, as found in Nature, and which in consequence code for peptides not normally found in any naturally occurring plant virus. The invention described therein comprises assembled particles of a plant virus containing a foreign peptide. The plant viruses described therein are therefore modified forms of the native viruses and for convenience will be referred to as modified viruses. The present invention concerns the same modified viruses.

The foreign peptide which may be incorporated into plant viruses according to our prior application WO 92/18618 may be of highly diverse types and are subject only to the limitation that the nature and size of the foreign peptide and the site at which it is placed in or on the virus particle do not interfere with the capacity of the modified virus to assemble when cultured in vitro or in vivo.). In this specification the term "foreign", as applied to a peptide or to the nucleic acid encoding it, signifies peptides or nucleic acid sequences which are not native to the plant virus used as a vector. Such sequences can be alternatively described as exogenous or heterologous sequences. The term "peptide" includes small peptides and polypeptides. The peptide preferably contains more than 5 amino acid residues. In broad concept, modified viruses may be formed from any biologically useful peptides (usually polypeptides) the function of which requires a particular conformation for its activity. This may be achieved by association of the peptide with a larger molecule, eg. to improve its stability or mode of presentation in a particular biological system. Examples of such peptides are peptide hormones; enzymes; growth factors; antigens of protozoal, viral, bacterial, fungal or animal origin; antibodies including anti-idiotypic antibodies; immunoregulators and cytokines, eg interferons and interleukins; receptors; adhesins; and parts or precursors of any of the foregoing types of peptide.

Among the broad range of bioactive peptide sequences presented on plant virus vectors in accordance with WO 92/18618 special importance attaches to the antigenic peptides which are the basis of vaccines, particularly animal (including human) virus vaccines. It should be noted that in the context of WO 92/18618 vaccines may have prophylactic (i.e. disease prevention) or therapeutic (i.e. disease treatment) applications. For vaccine applications WO 92/18618 provides an especially attractive epitope presentation system. When used for such applications the antigenic peptide component will be sited appropriately on the virus particle so as to be easily recognised by the immune system, for example by location on an exposed part of the coat protein of the virus. As applied to the latter, therefore, WO 92/18618 preferably provides assembled particles of a modified plant virus containing an antigen derived from a pathogen, eg an animal virus, incorporated in an exposed position on the surface of the coat protein of the plant virus. The present invention also relates the use of such assembled modified plant virus particle as the immunogenic component of a vaccine. Such assembled modified plant virus particles presenting antigenic peptides also have applications as the antigen presentation component of an immunodiagnostic assay for detection of eg. animal (including human) pathogens and diseases.

The system described in WO 92/18618 is highly versatile in regard to the size of the foreign peptide which may be inserted into the viral coat protein. Thus peptides containing up to 38 or more amino acids have been successfully inserted in the course of our continuing research.

The first aspect of the present invention relates to assembled particles of a plant virus containing a predetermined foreign peptide as part of the coat protein of the virus.

However, the modified viruses so produced, being non-natural structures, are at a competitive disadvantage with the unmodified virus (wild type) when propagated in plants. As a result, we have observed a tendency in some modified viruses for the foreign peptide to be lost during propagation with consequent reduction in yield of modified virus.

In accordance with our prior application WO 96/02649 (which is incorporated herein by reference), the causes of this problem have been identified and the steps necessary to avoid it have been determined.

Firstly, the process used for modifying the plant viral nucleic acid by introducing a nucleotide sequence coding for a foreign peptide should avoid the presence of direct sequence repeats flanking the insert. In the context of the present invention a construct containing a direct sequence repeat is one in which an identical oligonucleotide sequence is present on both sides of the inserted nucleotide. Such constructs can be genetically unstable because recombination can occur between the sequence repeats leading to loss of the foreign peptide coding sequence and reversion to the wild type sequence. Secondly, where the foreign oligonucleotide sequence is inserted into the plant virus genome as a substitution for part of the existing sequence, the resultant modified viral coat protein may be missing in an amino acid sequence which is important for virus replication, encapsidation and spread in the plant This defect may be readily determined and avoided. Thirdly, the heterologous sequence should not be inserted at a sub-optimal site.

With reference to the above modification, a second aspect of the present invention relates to assembled particles of a plant virus containing a foreign peptide insert in the coat protein of the virus, the site of the insert in the coat protein corresponding to a site in the plant virus genome which is free from direct sequence repeats flanking the insert. Preferably the insert is an addition at a non-terminal site in the coat protein.

The present invention can be applied to any plant virus, including both icosahedral and non-icosahedral plant viruses. A preferred group of plant viruses for use as vectors are those in which the nucleic acid coding for the capsid is a separate moiety from that which codes for other functional molecules and whose coat proteins have a β-barrel structure.

An advantage of the use of viruses which have a β-barrel structure is that the loops between the individual strands of β-sheet provide convenient sites for the insertion of foreign peptides. Modification of one or more loops is a preferred strategy for the expression of foreign peptides in accordance with the present invention.

To date, viruses from at least nine plant virus genera and three subgroup 2 ssRNA satellite viruses have had their tertiary and quaternary structures solved at high resolution. These are:

TABLE 1

| Name | Acronym | Genus | Family |
| --- | --- | --- | --- |
| Southern bean mosaic virus | SBMV | Sobemovirus | not assigned |
| Sesbania mosaic virus | SMV | Sobemovirus | not assigned |
| Tomato bushy stunt virus | TBSV | Tombusvirus | Tombusviridae |
| Turnip crinkle virus | TCV | Carmovirus | Tombusviridae |
| Cowpea chlorotic mottle virus | CCMV | Bromovirus | Bromoviridae |
| Alfalfa mosaic virus | AMV | Alfamovirus | Bromoviridae |
| Bean pod mottle virus | BPMV | Comovirus | Comoviridae |
| Cowpea mosaic virus | CPMV | Comovirus | Comoviridae |
| red clover mottle virus | RCMV | Comovirus | Comoviridae |
| Tobacco ringspot virus | TRSV | Nepovirus | Comoviridae |
| Turnip yellow mosaic | TYMV | Tymovirus | not assigned |
| Tobacco necrosis virus | TNV | Necrovirus | Tombusviridae |
| satellite tobacco necrosis virus | | Subgroup 2 | |
| satellite panicum mosaic virus | | Subgroup 2 | |
| satellite tobacco mosaic virus | | Subgroup 2 | |

All plant viruses possessing icosahedral symmetry whose structures have been solved conform to the eight stranded β-barrel fold as exemplified by cowpea mosaic virus, and it is likely that this represents a common structure in all icosahedral viruses. All such viruses are suitable for use in this invention for the presentation of foreign peptide sequences, preferably in the loops between the β-strands.

Preferred icosahedral plant viruses include all members of the following virus families: Caulimoviridae, Bromoviridae, Comoviridae, Geminiviridae, Reoviridae, Partitiviridae, Sequiviridae, Tombusviridae, and the following virus genera: Luteovirus, Marafivirus, Sobemovirus, Tymovirus, Enamovirus and Idaeovirus. Of the Tombusviridae family, the following genera are mentioned in particular: Dianthovirus, Machlomovirus and Necrovirus. An advantage of the Comoviridae and Sequiviridae is that their capsid contains sixty copies each of 3 different β-barrels which can be individually manipulated. All other virus families and genera listed above have similar 3-dimensional structures but with a single type of β-barrel. Viruses selected from the family Comoviridae (e.g. cowpea mosaic virus (CPMV), and bean pod mottle virus) are particularly preferred. CPMV is the most preferred virus.

In a particularly preferred embodiment the plant virus is cowpea mosaic virus (CPMV) and the foreign insert is made immediately preceding the proline 23 (Pro$^{23}$) residue in the βB–βC loop of the small capsid protein (VP23).

The present invention can also be applied to those β-barrel containing icosahedral plant viruses whose crystal structures have not yet been determined. Where significant sequence homology within the coat protein genes exists between one virus whose crystal structure is unknown and a second virus whose crystal structure has been determined, alignment of the primary structures will allow the locations of the loops between the β-strands to be inferred [see Dolja, V. V. and Koonin, E. V. (1991) J. Gen. Virol., 72, pp 1481–1486]. In addition, where a virus has only minimal coat protein sequence homology to those viruses whose crystal structure has been determined, primary structural alignments may be used in conjunction with appropriate secondary and tertiary structural prediction algorithms to allow determination of the location of potential insertion sites. The above application of the present invention is demonstrated in Examples 8 and 9.

A 3.5 Å electron density map of CPMV (see FIG. 1 in WO 92/18618) shows the clear structural relationship between the capsids of CPMV and the T=3 plant viruses, for example the bromoviruses, in particular cowpea chlorotic mottle virus (CCMV) and the sobemoviruses, in particular southern bean mosaic virus (SBMV). The capsids of these latter viruses are composed of 180 identical coat protein subunits, each consisting of a single β-barrel domain. These domains can occupy three different positions, namely A, B and C, within the virions (see FIG. 1 in WO 92/18618). The two coat proteins of CPMV were shown to consist of three distinct β-barrel domains, two being derived from the large capsid protein and one from the small capsid protein. Thus, in common with the T=3 viruses, each CPMV particle is made up of 180 β-barrel structures. The single domain from the small subunit occupies a position analogous to that of the A type subunits of CCMV and SBMV and other viruses, whereas the N- and C-terminal domains of the large capsid protein occupy the positions of the C and B type subunits respectively (see FIG. 1 in WO 92/18618).

X-ray diffraction analysis of crystals of CPMV and bean pod mottle virus (BPMV) shows that the 3-D structures of BPMV and CPMV are very similar and are typical of the Comoviridae in general.

In the structures of CPMV and BPMV, each β-barrel consists principally of 8 strands of antiparallel β-sheet connected by loops of varying length. The connectivity and nomenclature of the strands is given in FIG. 2 of WO 92/18618. The flat β-sheets are named the B,C,D,E,F,G,H and I sheets, and the connecting loops are referred to as the βB–βC, βD–βE, βF–βG and βH–βI loops.

One difference between the Comoviridae and the animal Picornaviridae is that the protein subunits of Comoviridae lack the large insertions between the strands of the β-barrels found in Picornaviridae. The four loops (βB–βC, βD–βE, βF–βG and βH–βI—see FIG. 3 in WO 92/18618) between the β-sheets are suitable for expression of foreign peptides such as tumour-associated mucin peptide sequences.

The βB–βC loop in the small capsid protein is particularly preferred as the insertion site. This loop has an engineered AatII site and a unique Nhe1 site at position 2708 of the M RNA-specific sequence where foreign peptide sequences may be inserted (see FIG. 4 of WO 92/18618). The insertion site immediately preceding Pro$^{23}$ in the βB–βC loop of the small capsid protein is most preferred.

The present invention is equally applicable to non-icosahedral plant viruses and any of these viruses may be manipulated for the expression of peptides or polypeptides in accordance with the present invention. There are nine genera and one family of positive sense RNA rod-shaped plant viruses which do not possess icosahedral particle morphology. There are two types of rod shaped virus, rigid rods and flexuous rods. The genera containing rigid rods are: Tobamovirus, Tobravirus, Hordeivirus and Furovirus. The genera and family containing flexuous rods are: Potexvirus, Capillovirus, Trichovirus, Carlavirus, Closterovirus and Potyviridae. Preferred embodiments are: tobamoviruses, in particular tobacco mosaic virus (TMV) and sunn-hemp mosaic virus (SHMV); tobraviruses, in particular pea early browning virus (PEBV), pepper ringspot virus (PepRSV) and tobacco rattle virus (TRV); Potexviruses, in particular potato virus X (PVX), white clover mosaic virus (WCIMV) and clover yellow mosaic virus (CIYMV), Potyviruses, in particular potato virus Y (PVY), plum pox virus (PPV) and tobacco etch virus (TEV).

The structure of the tobamovirues has been resolved to atomic resolution (by X-ray fibre diffraction) and it is to be assumed that the general architecture of the coat protein subunits of all rod shaped viruses are similar, differing only in the lengths and organisation of the N- and C-terminal extensions which protrude from the surface of the particle (Shukla et al. 1988). Application of the present invention to non-icosahedral plant viruses, the tertiary and quaternary structures of which are known to varying degrees, is demonstrated in Examples 10 to 13. As discussed above with reference to icosahedral plant viruses, the use of structural algorithms may be employed to identify potential insertion sites in non-icosahedral plant viruses whose crystal structures have not yet been determined.

To produce the modified plant virus particles in accordance with the first aspect of this invention the plant viral nucleic acid is modified by introducing a nucleotide sequence coding for the foreign peptide eg. an animal virus antigen at that part of the plant viral genome which codes for the coat protein, infecting plants or plant cells with the modified viral nucleic acid, and harvesting assembled particles of the modified virus. Preferably, the nucleic acid sequence encoding the foreign peptide is introduced at the part of the plant virus genome which codes for an exposed portion of the coat protein. This procedure is best carried out by direct manipulation of the DNA of the virus in the case of DNA viruses or by manipulation of a cDNA corresponding to the RNA of an RNA virus. In the case of an RNA virus, an RNA transcript of the modified DNA is usually prepared for inoculation of plant cells or preferably whole plants so as to achieve a multiplication stage prior to the harvesting of assembled particles of the modified virus. Alternatively, cDNA clones of RNA viruses may be constructed in plasmids such that 5' ends of the viral coat protein encoding sequences are abutted directly to the transcriptional start site of a promotor active in the plant host (see Example 6). In the case of a DNA virus, the DNA itself is introduced into the plant. In this way, the foreign peptide is initially expressed as part of the capsid protein and is thereby produced as part of the whole virus particle. The peptide may thus be produced as a conjugate molecule intended for used as such. Alternately, the genetic modification of the virus may be designed in order to permit release of the desired peptide by the application of appropriate agents which will effect cleavage from the virus particle.

In order to produce modified virus on a commercial scale, it is not necessary to prepare ineffective inoculant (DNA or RNA transcript) for each batch of virus production. Instead, an initial inoculant may be used to infect plants and the resulting modified virus may be passaged in the plants to produce whole virus or viral RNA as inoculant for subsequent batches.

The foreign RNA or DNA may be inserted into the plant virus genome in a variety of configurations. For example, it may be inserted as an addition to the existing nucleic acid or as a substitution for part of the existing sequence, the choice being determined largely by the structure of the capsid portion and the ease with which additions or replacements can be made without interference with the capacity of the genetically-modified virus to assemble in plants. Determination of the permissible and most appropriate size of addition or deletion for the purposes of this invention may be achieved in each particular case by experiment in the light of the present disclosure. The use of additional inserts appears to offer more flexibility than replacement inserts in some instances.

In accordance with this invention, multiplication of modified virus and production of significant yields thereof in plant hosts is an important part of the novel strategy of the invention, in particular to produce antigens for vaccines and other types of peptide in an advantageous manner. As indicated above, the inserted heterologous nucleotide sequence may include those coding for amino acids which are readily cleaved so that, after a multiplication stage, the desired material may be separated from the virus particles. As an alternative to total cleavage of the peptide, it may be possible and desirable in some cases to release the peptide in a form in which it remains intact within a major part of the capsid but separated from the viral nucleic acid.

According to the second aspect of the present invention, two different restriction enzyme sites are chosen within the viral nucleic encoding the coat protein and the nucleic acid is cleaved using the appropriate restriction enzymes. Pairs of complementary oligonucleotides are synthesised encoding the foreign peptide which it is desired to insert into the virus coat protein. The oligonucleotides terminate in ends which are compatible with the restriction enzymes sites thus allowing insertion into the cleaved virus nucleic acid. This procedure results in the introduction of a nucleotide sequence coding for a foreign peptide whilst avoiding the presence of direct sequence repeats flanking the insert. Complementary oligonucleotides are synthesised in which the sequence encoding the heterologous amino acids are flanked by plant virus-specific sequences so that the foreign nucleic acid is inserted as an addition to the existing nucleic acid.

The coat proteins of a number of the viruses indicated in Table 1 has been compared. The similarity of the secondary structural elements and their spatial organisation is illustrated in FIG. 10. Any of the loops which lie between the β-strands can be used for insertion of foreign epitopes, however the insertions are made such that the additions are exposed on either the internal or external surface of the virus and such that assembly of the coat protein subunits and the infectivity of the virus are not abolished. The choice of a particular loop can be made using knowledge of the structure of individual coat protein subunits and their interactions with each other, as indicated by the crystal structure, such that any insertions are unlikely to interfere with virus assembly. The choice of precise insertion site can be made, initially, by inspection of the crystal structure, followed by in vivo experimentation to identify the optimum site.

In a preferred embodiment the three dimensional structure of a plant virus is examined in order to identify portions of a coat protein which are particularly exposed on the virus surface and are therefore potentially optimum sites for insertion. In a further embodiment the amino acid sequence of the exposed portion of a coat protein is examined for amino acids which break α-helical structures because these are potentially optimum sites for insertion. Examples of suitable amino acids are proline and hydroxyproline, both of which whenever they occur in a polypeptide chain interrupt the α-helix and create a rigid kink or bend in the structure.

To demonstrate this system, the plant virus cowpea mosaic virus (CPMV) was chosen. The three-dimensional structure of CPMV has been solved at atomic resolution which has enabled identification of sites suitable for modification without disruption of the particle structure. CPMV comprises two subunits, the small (S) and the large (L) coat proteins, of which there are 60 copies of each per virus particle. Foreign peptide sequences may be expressed from either the L or S proteins or from both coat proteins on the same virion. Thus, up to 120 copies of the foreign peptide sequence may be expressed from a single virus particle.

Various sites in the CPMV coat protein have been identified as suitable for insertion of the foreign peptide. The co-ordinates given below refer to the linear amino acid sequence of the CPMV coat protein (S or L subunit).

Any insertion site which does not lie between the N-terminus of a subunit and a β-strand, or between a β-strand and the C-terminus, is considered to lie between two β-strands. Such an insertion site may lie in a short loop at one of the axes of symmetry of the virus or in one of the much longer connecting strands which form the body of the protein subunits and which may contain additional secondary structure and form loops on the surface of the virus. In particular, there are α-helices present in some of the connecting strands which form the body of the protein subunits, and the co-ordinates given for some of the insertion sites may indicate that an α-helix is present between the insertion site and the preceding or succeeding β-strand. For example, the S protein C' and C" β-strands represent a secondary structure formed in the loop between the βC and βD strands.

(i) External Surface Sites

S Subunit (A Domain) Insertion Sites

βB–βC:

The residues between the β-strands are Thr 19 to Val 22, and the preferred insertion site is between amino-acids 22 and 23. Insertion sites either side of this are also suitable, notably between residues 21 and 22.

βC'–βC":

The residues between the β-strands are Val 42 to Asn 46.

βH–βI:

This site is at the tip of the five-fold axis and the residues between the β-strands are Thr 152 to Gln 158.

βD–βE:

Again, this site is at the tip of the five-fold axis and the residues between the β-strands are Ala 80 to Gln 90.

βE–βF:

This site is not at the tip of the five-fold axis, but lies 'behind' and to one side of the β-strands.

The residues between the β-strands are Arg 96 to Ala 106. Residues 98 to 102 are preferred.

L Subunit, B Domain Insertion Sites

The B domain of the L subunit comprises amino acids 183–374 of the linear amino-acid sequence.

βB–βC:

This site is in the equivalent location on the subunit to the standard S protein insertion site and is at the three-fold axis of the virus. The residues between the β-strands are Pro 201 to Glu 209.

βH–βI:

Again this site is at the three-fold axis of the virus and the residues between the β-strands are His 331–Asp 341.

βC–αA (βC–βD):

This site lies between the βC and βD strands. The protein chain loops out to form part of the body of the protein domain. Within this loop is an α-helix (termed αA) and the insertion site is a surface exposed portion which lies between the βC strand and the αA helix. The surface exposed residues are Ala 223 to Ala 226.

βG–αD (βG–βH):

This site lies between the βG and βH strands. The protein chain loops out to form part of the body of the protein domain. Within this loop is an α-helix (termed αD) and the insertion site is a surface portion which lies between the αD helix and βH strands which are surface exposed. The surface exposed residues are Pro 314 to Thr 317.

βE–αB (βE–βF):

This site lies between the βE and βF strands. The protein chain loops out to form part of the body of the protein domain. Within this loop is an α-helix (termed αB) and the insertion site is a surface portion which lies between the βE strand and the αB helix. The surface exposed residues are Gly 269 to Phe 275.

L subunit, C Domain Insertion Sites

The C Domain of the L Subunit comprises amino-acids 1–182 of the linear amino-acid sequence.

βE–αB (βE–βF):

This site lies between the βE and βF strands. The protein chain loops out to form part of the body of the protein domain. Within this loop is an α-helix (termed αB) and the insertion site is a surface exposed portion which lies between the βE strand and the αB helix. The surface exposed residues are Gly 95 to Thr 102.

αD–βH (βG–βH):

This site lies between the βG and βH strands. The protein chain loops out to form part of the body of the protein domain Within this loop is an α-helix (termed αD) and the insertion site is a surface portion which lies between the αD helix and the βH strands. The surface exposed residues are Ser 142 and Arg 145.

βC–αA (βC–βD):

This site lies between the βC and βD strands. The protein chain loops out to form part of the body of the protein domain. Within this loop is an α-helix (termed αA) and the insertion site is a surface exposed portion which lies between the βC strand and the αA helix. The surface exposed residues, not part of any secondary structural element, are Gly 53 to Phe 56.

βB–βC:

This site is an equivalent location on this domain to the S protein βB–βC (identified above) insertion site and is at the three-fold axis of the virus. The residues between the β-strands are Ser 33 to Leu 42.

(ii) Internal Surface Sites

S Subunit (A Domain) Insertion Sites

βG–βH:

This protein chain between β-strands points in towards the interior of the virus and forms a 'double loop'. One insertion site comprises residues Pro 128 to Ser 130.

L Subunit B Domain Insertion Sites

βF–βG:

This loop is at the three-fold axis symmetry of the virus, and is the bottom loop of the four. The residues in the loop are Gln 287 to Glu 293.

C Domain β1–B Domain βB:

This is the junction between the B and C domains of the L subunit. This linker sequence comprises residues Asn 374 to Asp 186. The insertion site is around Ala 185, which is assigned to the B domain.

L Subunit, C Domain Insertion Sites

βG–αD (βG–βH):

This site lies between the βG and βH strands. The protein chain loops out to form part of the body of the protein domain. Within this loop is an α-helix (termed αD) and the insertion site is an internal projecting loop which lies between the βG strands and the αD helix. The residues in this loop are Asn 130 to Ser 135.

CPMV is biparite RNA virus and in order to manipulate the genome of any RNA virus to express foreign peptides it is necessary to use cDNA clones of the RNA. Full length cDNA clones of both CPMV RNA molecules are available which can be manipulated to insert oligonucleotide sequences encoding a foreign peptide. cDNA clones of the genome from plant RNA viruses can be used to generate in vitro transcripts that are infectious when inoculated onto plants. However, the infectivity of the transcripts is significantly lower than that of natural virion RNAs, probably as a result of the presence of non-viral residues at the termini of the transcripts. Difficulties may also be caused by exposure of the transcripts to degradative agents during inoculation. For this reason, the transcripts are usually stabilised by capping their 5' ends, but this is an inefficient, costly and time-consuming process.

In a further aspect of the present invention, cDNA clones of CPMV RNAs M and B have been constructed, in which the cDNA clone of the M RNA contains an inserted oligonucleotide sequence encoding a foreign peptide, which make use of the cauliflower mosaic virus (CaMV) 35S promoter sequence linked to the 5' ends of the viral cDNAs to generate infectious transcripts in the plant. This technique overcomes some of the problems encountered with the use of transcripts generated in vitro and is applicable to all plant RNA viruses.

To demonstrate the wide applicability of this invention, antigenic peptides from four different animal viruses, one bacterial pathogen of animals and a mammalian peptide hormone were used. Two of the viruses belong to the picornavirus group of animal viruses—foot and mouth disease virus (FMDV) and human rhinovirus (HRV). There are several important pathogens in this group, particularly, FMDV, poliomyelitis (polio) and hepatitis A. The third virus selected is human immune deficiency virus (HIV) which bears no similarity to any known plant virus, and for which no successful vaccines are currently available. The bacterial pathogen is *Staphylococcus aureus*, a causative agent of several animal diseases including mastitis in cows. The peptide hormone is porcine gonadotrophin releasing hormone.

The present invention will now be described with reference to the following Examples and accompanying drawings. No limitation thereto is intended:

BRIEF DESCRIPTION OF THE DRAWINGS

FIG. 1 SEQ ID NOS: 1 and 2 depicts the region of CPMV M RNA which encodes the amino-terminal 40 amino acids of VP23. The numbers below the nucleotide refer to the M RNA sequence and the position of the unique Nhe1 site is indicated. The amino acids involved in forming the βB and βC strands of VP23 are indicated above the amino acid sequence of the protein which is shown using the standard one-letter code.

FIGS. 2a and 2b depicts (A) the sequence of the oligonucleotide used in the construction of pFMDV together with the amino acid sequence encoded by the top (positive) strand, which corresponds to amino acid residues 136–160 from VP1 of FMDV serotype $O_1$, and (B) the structure of VP23 after insertion of the FMDV-specific oligonucleotides. The arrowed region indicates the extent of the inserted FMDV epitope. The Nhe1 site not restored during the cloning is indicated by xNhe1. The diagnostic Bgl II site present in the inserted sequence is also indicated.

FIG. 3 SEQ ID NOS: 8 to 10 depicts the effect of insertion of the FMDV-specific oligonucleotides, encoding amino acid residues 136–160 from VP1 of FMDV serotype $O_1$, on the structure of VP23 in pMT7-FMDV-I. The amino acids involved in forming the βB and βC strands of VP23 are indicated above the amino acid sequence of the protein which is shown using the standard one-letter code.

FIGS. 5a and 5b depicts (A) the nucleotide sequence if the oligonucleotides used in the construction of pMT7-HIV together with the amino acid sequence encoded by the top (positive) strand which corresponds to amino acid residues 735–752 from gp41 of HIV1, and (B) the sequence of VP23 after insertion of the HIV-specific oligonucleotides. The arrowed region indicates the extent of the inserted HIV epitope. The Pvu 1 site present in the inserted sequence is also indicated.

FIGS. 6a and 6b depicts (A) the nucleotide sequence if the oligonucleotides used in the construction of pMT7-HRV together with the amino acid sequence encoded by the top (positive) strand which corresponds to amino acid residues 85–99 from VP1 of HRV-14, and (B) the sequence of VP23 after insertion of the HRV-specific oligonucleotides. The arrowed region indicates the extent of the inserted HRV epitope. The Cla 1 site present in the inserted sequence is also indicated.

FIG. 7 SEQ ID NOS: 24 to 26 depicts the effect of insertion of the FMDV-specific oligonucleotides, (depicted in bold type) encoding amino acid residues 141–160 from VP1 of FMDV serotype $O_1$, on the sequence of VP23 in pMT7-FMDV-II.

FIG. 8 SEQ ID NOS: 27 to 41: Sequence of the oligonucleotides used to construct pMT7-FMDV, pMT7-HRV-II and pMT7-HIV-III. All oligonucleotides used terminated in the sequences shown in bold at the top of the diagram. The variable portions used for the construction of pMT7-FMDV-V (FMDV-V), pMT7-HRV-II (HRV-II) and pMT7-HIV-III (HIV-III) are shown below. The amino acid sequences encoded by the plus-sense oligonucleotides are indicated above the nucleotide sequence and correspond as follows: FMDV-V, amino acids 141–160 SEQ ID NO: 33 from VP1 of FMDV serotype $O_1$, HRV-II amino acids 85–98 SEQ ID NO: 36 from VP1 of HRV-14; HIV-III, amino acids 731–752 SEQ ID NO: 39 from gp41 of HIV-1.

FIGS. 11a and 11b shows the (A) nucleotide and (B) protein sequences of SBMV surrounding a potential insertion site.

FIG. 12 shows a comparison of the βH–βI loop of three sobemoviruses. Conserved residues are highlighted in bold and the locations of the loops and β-strands are indicated.

FIGS. 13a and 13b shows the (A) nucleotide and (B) protein sequences of LTSV surrounding a potential insertion site.

FIG. 14 illustrates alignment of the coat protein sequences of RCNMV and TBSV using a Lopman-Person alignment algorithm.

FIG. 16 illustrates application of the EMBL PHDsec algorithm program to the same RCNMV sequence as shown in FIG. 15.

FIGS. 17a and 17b shows the (A) nucleotide and (B) protein sequences of RCNMV surrounding a potential insertion site.

FIGS. 18a and 18b shows B) five deletion constructs and (A) an unmodified clone of TRV as described in Example 13.

Modification of CPMV

Figure 4:
FIG. 4 SEQ ID NOS: 11 to 13 depicts the construction of a "substitution" vector by site-directed mutagenesis. The asterisk indicates the T residue that is changed to a C by site-directed mutagenesis, thereby creating a novel AatII site.

Methods for manipulating the genome of the virus in order to make insertions into the coat of CPMV are described in WO 92/18618 and in WO 96/02649. A full length cDNA clone of CPMV M RNA in transcription vector pPMI is available (pPMM2902), as is a full length cDNA clone of CPMV (pBT7-123). A mixture of transcripts from pPMM2902 and pBT7-123 gives rise to a full virus infection when electroporated into cowpea protoplasts.

We have selected the βB–βC loop in VP23 for the insertion of foreign peptide. This loop is clearly exposed on the surface of the viral particle and computer modelling has shown that even large loops inserted at this site are unlikely to interfere with the interaction between adjacent subunits responsible for capsid structure and stability. This loop has a unique Nhe1 site at position 2708 M RNA-specific sequence where foreign sequences may be inserted (see FIG. 1).

The principal antigenic sites of the picornavirus foot and mouth disease (FMDV) and human rhinovirus (HRV), and the lentiretrovirus human immune deficiency virus (HIV) were used to illustrate the use of modified plant viruses in the production of vaccines to animal viruses.

The design and construction of pFMDV, a full length cDNA clone of CPMV M RNA containing an insert coding for a segment of FMDV loop protein, is described in WO 92/18618. An oligonucleotide sequence encoding amino acid residues 136–160 from VP1 of FMDV serotype $O_1$ strain BFS 1860 was inserted into the unique Nhe1 site of pPMM2902 as an addition to the existing nucleic acid. The procedure used resulted in the creation of a direct repeat sequence flanking the insert (see FIG. 2B). The properties of pFMDV transcripts are described in WO 92/18618. Infection of cowpea protoplasts with a mixture of pFMDV and pBT7-123 transcripts leads to multiplication and assembly of modified virus particles.

However, to produce modified plant viruses on a large scale it is necessary to prepare a construct which can be inoculated directly onto whole plants, and which will replicate and assemble into virus particles as in the protoplast system. Therefore pPMM2902 was modified such that RNA synthesis is driven by a more efficient promoter and the modified plasmid transcribed under conditions that result in the transcripts having a "cap" structure at their 5' ends. The steps in the modification of pPMM2902 to produce pMT7-601 are described in detail in WO 92/18618. A mixture of capped pMT7-601 and pBT7-123 transcripts was found to be infectious to intact cowpea plants.

The design and construction of pMT7-FMDV-I, starting from pMT7-601 and pFMDV, are described in WO 92/18618. An oligonucleotide sequence encoding amino acid residues 136–160 VP1 of FMDV serotype $0_1$, was inserted into the unique Nhe1 site of pMT7-601 as an addition to the existing nucleic acid. The procedure used resulted in the creation of a direct repeat sequence flanking the insert (see FIG. 3). The properties of pMT7-FMDV-I transcripts are described in detail in Usha, et al. [Virology (1993) 197, 366–374]. Plants inoculated with a mixture of pMT7-FMDV-I and pBT7-123 transcripts developed lesions on their inoculated leaves which were smaller than those seen on the leaves of plants inoculated with wild type transcripts. Immunosorbent electron microscopy on leaf homogenates from inoculated leaves of pMT7-FMDV-I-infected plants confirmed the presence of CPMV-like virus particles. However, there was no evidence of systemic spread of the chimaeric virus particles to uninoculated leaves.

We have since characterised the progeny of a pMT7-FMDV-1 infection by reverse transcriptase-polymerase chain reaction (RT-PCR) analysis of RNA extracted from leaves inoculated with pMT7-FMDV-1. The analysis revealed the presence of two products, the major one corresponding to the expected product of approximately 580 bp and a minor one of 500 bp. The latter product comigrated with the product synthesised from RNA extracted from a plant infected wild-type CPMV. When the PCR products were cloned into bacteriophage M13 and the sequence around the site of insertion was determined, two classes of clones could be found: those which retained the entire FMDV-specific sequence (the majority) and those which contained a sequence corresponding exactly to wild-type CPMV (the minority). These results indicate that reversion to the wild-type sequence occurs in the transcript-inoculated leaves by an apparently single-step process.

When RNA extracted from a pMT7-FMDV-1 transcript-inoculated leaf was passaged on to uninfected cowpeas, the plants developed symptoms on their inoculated leaves which consisted of a mixture of small lesions characteristic of a pMT7-FMDV-1 infection and larger wild-type CPMV lesions. In addition, the upper leaves developed mosaic symptoms characteristic of a wild-type CPMV infection. RT-PCR analysis of RNA extracted from the inoculated leaves of such again yielded two products but in this case the dominant one corresponded to that derived from wild-type M RNA. Analysis of clones derived from the dominant mixture of PCR products again revealed the same two classes of sequence found previously. However, in this case the majority of clones represented the wild-type sequence. These results indicate that not only does pMT7-FMDV-1 tend to lose the entire FMDV-specific sequence in a single step process, probably as a result of the presence of direct repeats flanking the insert but also that wild-type progeny hove a significant advantage over the chimaeric virus.

In order to avoid the creation of a direct repeat sequence flanking the insert, a second restriction enzyme cutting site was created in the nucleotide sequence of the region of the CPMV genome encoding VP23. A single silent base change (U to C) at position 2740 of the M RNA creates a unique AatII site at amino acid valine 27 (position 2735 of the nucleotide sequence). This was achieved by site-directed metagenesis of M13-JR-1 using methods described in WO 92/18618 (see FIG. 4). The creation of the AatII site enables the nucleotide sequence encoding the six amino acids from the native βB–βC loop in CPMV to be removed by digestion with Nhe1 and AatII. The sequence can then be replaced by any sequence with Nhe1- and AatII-compatible ends.

Construction of pMT7-FMDV-II, pMT7-HIV and pMT7-HRV

Three different sequences were designed to be substituted for the sequence between the Nhe1 and AatII sites of the mutated M RNA sequence. In all three cases the foreign sequences substituted for wild-type sequences encoding six amino acids. The first sequence to be substituted into VP23 consisted of oligonucleotides encoding residues 735–752 from the transmembrane glycoprotein gp41 from human immunodeficiency virus (HIV-1). This sequence was elected because a synthetic peptide for this region is recognised in enzyme-inked immunosorbent assays (ELISA) by antisera from seropositive AIDS patients and is capable of including antibodies which neutralise a range of HIV-1 isolates. The second sequence consists of the nucleotide sequence encoding residues 85–99 from VP1 of human rhinovirus 14 (HRV-14). In both cases, the oligonucleotides were designed to contain restriction enzyme sites to facilitate screening. The sequences of the oligonucleotides and the effect of the substitutions on the acid sequence of VP23 are shown in FIGS. 5 and 6. The methods used for the construction of pMT7-HIV and pMT7-HRV are given in WO 92/18618.

The third sequence consisted of nucleotides encoding residues 141–160 from VP1 of FMDV serotype $0_1$. The effect of the substitution on the amino acid sequence of VP23 is shown in FIG. 7. The method used for the construction of pMT7-FMDV-II is given in Usha, et al. (1993).

The properties of pMT7-HIV and pMT7-FMDV-II transcripts are described in WO 92/18618 and Usha, et al. (1993) respectively. pMT7-HIV transcripts, when mixed with pBT7-123 transcripts can replicate in cowpea protoplasts and the resultant modified coat protein can assemble into chimaeric virus particles. Similarly, pMT7-FMDV-II transcripts can replicate in cowpea protoplasts but progeny RNA accumulated at a considerably lower level than that from pMT7-FMDV-I, or from pMT7-601 which contains the wild-type VP23 sequence. No virus particles could be detected in protoplasts infected with pMT7-FMDV-II. The ability of transcripts derived from pMT7-FMDV-II to multiply in whole cowpea plants was also studied by Usha, et al. (1993).

No symptoms developed on inoculated plants and no progeny could be detected in either the inoculated or the upper leaves. The reduced infectivity of pMT7-FMDV-II may be attributed to the resultant chimaeric virus particles lacking an amino acid sequence which is present in the wild type virus, and in chimaeric virus produced from pMT7-FMDV-I infections, and is important for virus replication and spread in the plant.

EXAMPLE 1

Construction of pMT7-FMDV-V, PMT7-HRV-II and pMT7-HIV-III

The small lesion phenotype of pMT7-FMDV-1 and its competitive disadvantage in comparison with wild-type CPMV, suggest that the heterologous sequence may have been inserted at a sub-optimal site. Detailed examination of the 3-D structure of CPMV revealed that proline 23 ($Pro^{23}$), which lies in the centre of the βB–βC loop of the S protein, is particularly exposed on the virus surface and is potentially the optimum site for any insertion. To make use of this fact and to prevent the introduction of repeated sequences which may facilitate reversion, pairs of complementary oligonucleotides were synthesised in which the sequence encoding the heterologous amino acids are flanked by sequences present in wild type CPMV such that the insert is made immediately preceding $Pro^{23}$. The oligonucleotides terminate in Nhe1 and AatII compatible ends enabling them to be inserted between the Nhe1 and AatII sites of either pMT7-FMDV-II (Usha, et al. 1993) or its derivative pMT7-FMDV-II, AatII in place of the original FMDV-specific inserts. Such a strategy not only ensures that the heterologous sequences are inserted at the optimal site and that the inserts are not flanked by direct repeats but also ensures that no CPMV-specific sequences are deleted, a fact believed to be important in enabling virus particles to assemble (Usha, et al. 1993). The sequences inserted in this manner consisted of residues 141–159 of VP1 of FMDV serotype $0_1$ (a slightly shorter version of the epitope in pMT7-FMDV-I), residues 85–98 of VP1 of HRV-14 which make up the immunodominant site, Nlm-IA [Sherry, et al., J. Virology (1986) 57, 246–257], and an epitope comprising residues 731–752 from gp41 of HIV-1, the so-called "Kennedy epitope" [Kennedy, et al., Science (1986) 231, 1556–1559]. The sequence of the oligonucleotides used in the constructions is shown in FIG. 8. The resulting constructs were designated pMT7-FMDV-V, pMT7-HRV-II and pM7-HIV-III, respectively.

The construction and properties of plasmids pBT7-123, pMT7-FMDV-I and pMT7-FMDV-II have been described previously (Usha, et al., 1993). These constructs and their derivatives were propagated in *Escherichia coli* strain JM83. Oligonucleotides were synthesized on a Pharmacia GENE ASSEMBLER PLUS™ synthesizer. Sequence analysis was performed by "dideoxy" method using either *E. coli* DNA polymerase I (Klenow fragment) or Sequenase™ version 2.0.

To construct pMT7-FMDV-V, pMT7-FMDV-II was digested to completion with Nhe1 (which cleaves at position 2708 of the M RNA sequence) and partially with AatII which cuts once within M RNA sequence (position 2735) and once in the pUC-derived portion of the plasmid position 2617 on the pUC19 map). A pair of complementary oligonucleotides encoding residues 141–159 from VP1 of FMDV serotype $0_1$, flanked by sequences encoding residues 18–22 and 23–26 of the CPMV VP23 protein (FIG. 8) were phosphorylated, annealed and ligated into NheI/AatII-digested pMT7-FMDV-II. Recombinants having the desired structure were identified by restriction enzyme mapping and sequence analysis.

To construct pMT7-HRV-II and pMT7-HIV-III, pMT7-FMDV-II was initially partially digested with AatII and their full-length linear molecules recovered after agarose gel electrophoresis. The linearised plasmid was treated with *E. coli* DNA polymerase I (Klenow fragment) to remove the 3' overhangs left by AatII, recircularised and transformed back into *E. coli* strain JM83. A recombinant, designated pMT7-FMDV-AatII, in which the AatII site in the pUC portion of the plasmid had been destroyed but which retained the AatII site in the M RNA specific portion was identified by restriction enzyme analysis. Complementary oligonucleotides encoding residues 85–98 of VP1 of HRV-14 or residues 731–752 of gp41 of HIV-1, flanked by the appropriate CPMV-specific sequences were phosphorylated, annealed and ligated into NheII/AatII-digested pMT7-FMDV-AatII giving rise to pMT7-HRV-II and pMT7-HIV-III, respectively.

EXAMPLE 2

Ability of pMT7-FMDV-V, pMT7-HRV-II and pMT7-HIV-III to Replicate in Whole Cowpea Plants When RNA was transcribed from the chimaeric plasmids, mixed with transcripts from pBT7-123 and inoculated on to cowpea plants, in each case the inoculated leaves developed chlorotic lesions typical of a wild-type CPMV infection. RNA hybridisation analysis revealed the presence of M RNA-specific sequences within these leaves. In all three cases the infection could be mechanically transmitted to further healthy cowpea plants. In the case of pMT7-HRV-II and pMT7-HIV-III the infection spread to the upper leaves of most of the infected plants giving a typical systemic mosaic. However, the infection induced by pMT7-FMDV remained associated exclusively with the inoculated leaves, no systemic symptoms being observed and no viral-specific RNA being detected in the upper leaves of the plants.

When total RNA was extracted from leaves inoculated with pMT7-FMDV-V transcripts and analysed by RT-PCR, only a single band corresponding in size to the product derived from RNA retaining the insert was observed. Even after up to three serial passages, a similar result was obtained. To confirm that the insert had been retained, the products derived from samples taken from plants after initial inoculation and after three serial passages were cloned into bacteriophage M13 and the nucleotide sequence of a representative number of clones determined. All the clones in both instances contained the sequence corresponding to viral RNA which retained the inserted sequence intact. These results indicate that reversion of pMT7-FMDV-V RNA had not occurred at a detectable frequency. Analysis of RNA extracted from purified pMT7-HRV-II and pMT7-HIV-III particles (see below) supported the conclusion that the new constructs are genetically stable, no evidence of reversion being found after 10 serial passages.

Virus particles could be prepared from leaf tissue with either pMT7-HRV-II or pMT7-HIV-III using the standard CPMV purification protocol [van Kammen and de Jager (1978), Cowpea mosaic virus. *CMI/AAB Descriptions of Plant Viruses*, 197], the yields obtained (1.2–1.5 mg of virus per gram of fresh tissue) being similar to that obtained with wild-type CPMV. By contrast no particles derived from pMT7-FMDV-V could be obtained using the standard procedure or a number of variants of it. This failure was not due to the absence of particles within the infected tissue since large numbers of such particles could be seen by immunosorbent electron micoscopy (ISEM) of tissue homogenate using grids coated with anti-CPMV serum.

EXAMPLE 3

Immunological Properties of Chimaeric Virus Particles Derived from pMT7-HRV-II and pMT7-HIV-III To confirm that the purified pMT7-HRV-II particles possessed the antigenic properties of the inserted sequence, samples of the purified virions were subjected to western blot analysis using a polyclonal antiserum raised against HRV-14. A product corresponding in size to the modified VP23 protein could be detected, confirming the antigenicity of the inserted sequence. No reaction could be seen with the antiserum when samples of wild-type CPMV were analysed in the same way.

When a sample of denatured virus was examined by electrophoresis on a SDS-polyacrylamide gel, only three bands were seen. The largest polypeptide (L) corresponds to the large (VP37) viral coat protein and comigrated with the L polypeptide from wild-type CPMV. The middle band ($S_s$) corresponds to the small (VP23) viral coat protein barbouring the HIV-1-specific epitope. The fastest migrating band ($S^1$) represents the C-terminal 192 amino acids of the VP23 protein. Terminal sequence analysis showed that it was derived from the VP23 protein by proteolytic cleavage between the two C-terminal amino acid residues of the insert. Thus $S_s$, but not $S^1$, contains the insert and as predicted reacts with gp41-specific antibody by Western blotting. The predicted N-terminal cleavage product consists of only 43 residues and could not be resolved on the gel system used. Both elements of S remain associated with the virion. Because a certain amount of $S^1$ protein was always present in preparations of CPMV-HIV regardless of how quickly the virus was purified, it is possible that this cleavage occurs in planta.

The strategy designed to overcome the limitations of pMT7-FMDV-I has proved to be successful since all three of the new chimaera (pMT7-FMDV-V, pMT7-HRV-II land pMT7-HIV-III) gave wild-type symptoms on the inoculated leaves and showed no sign of reversion. Furthermore, two chimaera grew as well as wild-type CPMV and could be readily purified. The fact that pMT7-FMDV-V gives wild-type lesions on inoculated leaves but fails to spread systemically suggests that these chimaeric virus particles are fully competent for cell-to-cell movement but deficient for long-distant transport. This phenomenon may be related to the observation that particles from pMT7-FMDV-V appear to aggregate into intracellular crystalline arrays making purification problematic. These features are not a result of the length of heterologous sequence since pMT7-FMDV-V contains an insert intermediate in size (19 residues) between those contained in pMT7-HRV-II (14 residues) and pMT7-HIV-III (22 residues).

EXAMPLE 4

Use of Chimaeric pMT7-HRV-II Virus Particles to Raise Antibodies to HRV

Particles of pMT7-HRV-II and wild-type CPMV were purified as described in Example 2, injected into rabbits, the antisera collected and used to probe western blots of denatured HRV-14 virus particles. A single band corresponding to VP1 of HRV-14 could be detected using the antiserum raised against pMT7-HRV-II virus particles even when the serum was diluted 1:16,000. No reaction could be seen with the other HRV-14 coat proteins (VP2 and VP3). No reaction with any HRV-14 protein was found when serum raised against wild-type CPMV was used to probe the blots. The ability of pMT7-HRV-II virions to raise antibodies which recognise VP1 of HRV-14 shows that epitopes presented on the surface of CPMV particles are immunogenic.

EXAMPLE 5

Use of Chimaeric pMT7-HIV-III Virus Particles to Raise Neutralizing Antibodies to HIV Transcripts derived from pMT7-HIV-III were mixed with transcripts derived from plasmid pBT7-123 and inoculated onto the leaves of 10 day-old cowpea plants. To obtain large yields of recombinant virus particles, samples of leaf tissue showing symptoms characteristic of a CPMV infection were homogenised in 100 mM sodium phosphate pH7.0, centrifuged briefly and the supernatant used to inoculate healthy cowpea plants. The plants were harvested 2–3 weeks post-inoculation and chimaeric virus particles purified as described in Example 2. The purified chimaeric virus, designated CPMV-HIV-I, was stored at 4° C. in 10 mM sodium phosphate pH7.0 in the presence of 0.05% (w/v) sodium azide. The quality of the preparation was monitored by electron microscopy and by electrophoresis of portions of denatured virus on 15% polyacrylamide/SDS/reducing gels. The proteins were visualised by staining the gel with coomassie brilliant blue R250. Prior to injection into mice the virus preparation was dialysed against phosphate-buffered saline and protein concentration determined by Bio-Rad™ assay.

Adult C57/BL6 mice were immunized at 8 weeks of age. Virus (CPMV-HIV-I or CPMV) was mixed with aluminium hydroxide adjuvant at a ratio of 1:5 with stirring for 30 min at room temperature. Mice (6 per group) were immunized subcutaneously at the back of the neck in 5 sites with a total of 100 μl of virus-adjuvant mixture containing 100 μg virus. At the required intervals animals were bled from the tail, and serum stored at −20° C. All sera were heated at 56° C. for 30 min before being assayed for neutralizing antibody.

Mice were given two injections of CPMV-HIV-1 or wild type CPMV at 0 and 35 days and bled from the tail 14 days later. Individual neutralizing titres of HIV-1 IIIB were determined as follows. Dilutions of heat-treated serum were incubated with about 2000 syncytium-forming units (sfu) per ml of virus for 1 h at 37%. Semiconfluent monolayers of C8166 cells ($5 \times 10^4$ cells/well) were prepared in 96-well tissue culture plates, which had been pretreated with poly-L-lysine. Medium was removed and the cells received 50 µl of inoculum. These were incubated for 1 h at 37° C. before fresh medium was added. Incubation was continued for 3 days at 37° C., and syncytia were counted with the aid of a microscope and the percentage inhibition calculated for each well.

Figure 9:
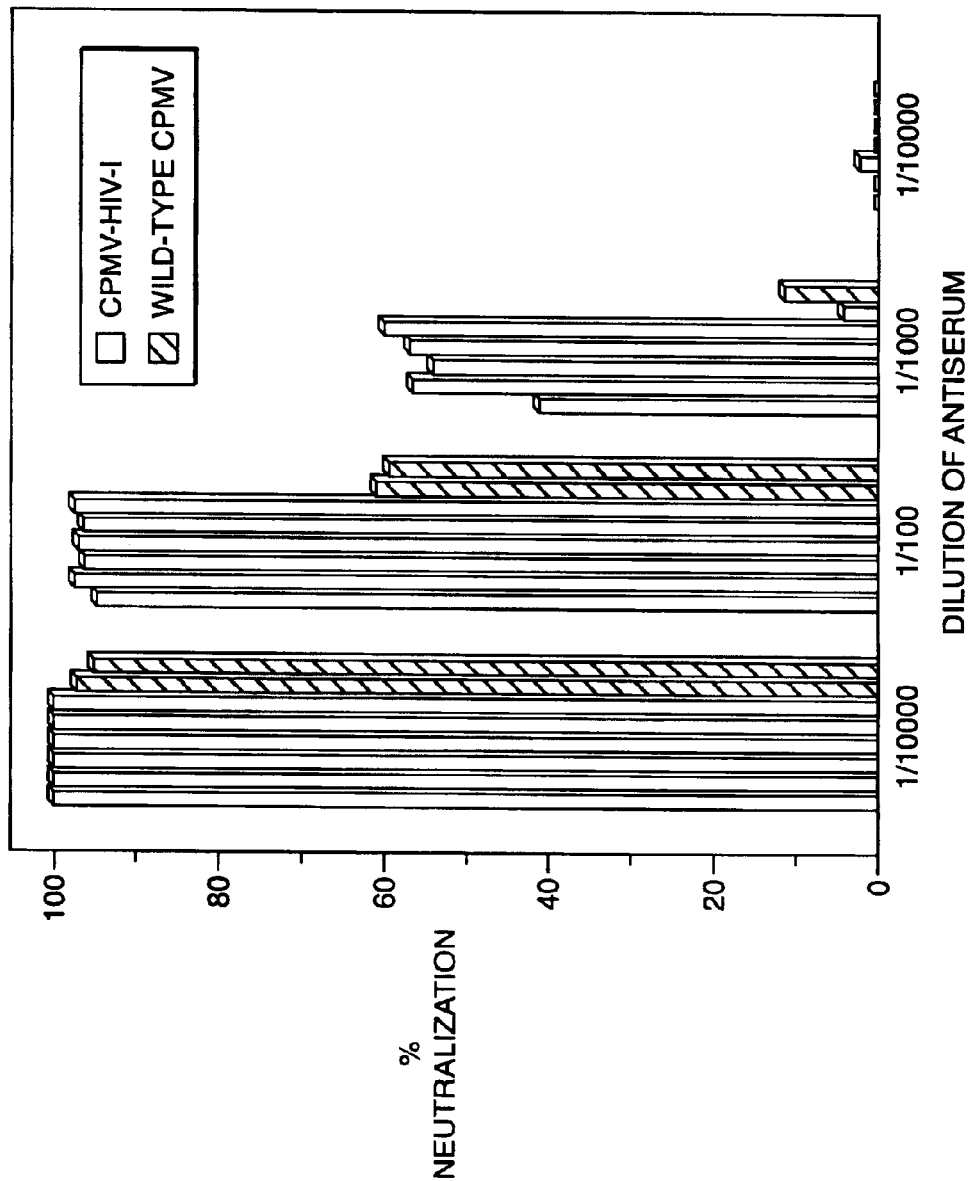
FIG. 9 Neutralization of HIV-1 IIIB by sera from individual C57/BL6 mice given two sub-cutaneous injections of the CPMV-HV-I chimaera expressing amino acids 731–752 of gp41 on its surface (open bars). Mice were bled after 14 days. Also shown is the mean serum neutralization titre of a parallel group of mice inoculated with wild type CPMV (solid bars). All immunogens were formulated in alum adjuvant.
Figure 10A:
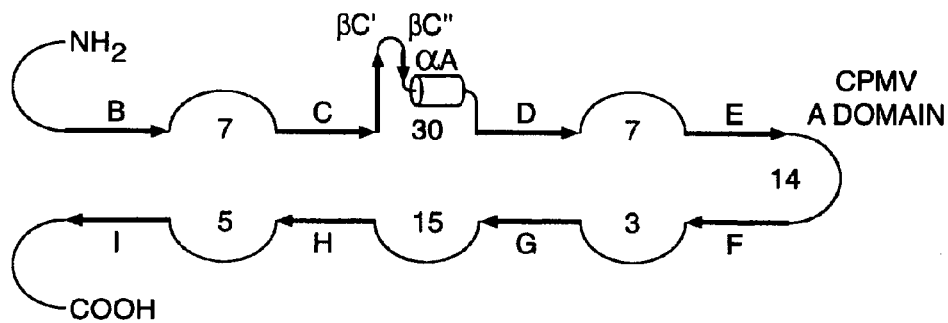
FIG. 10 (Parts A–T) is a simple line drawing of the solved β-barrel containing virus structures showing the secondary structural elements which make up the coat protein domains.
Figure 10B:
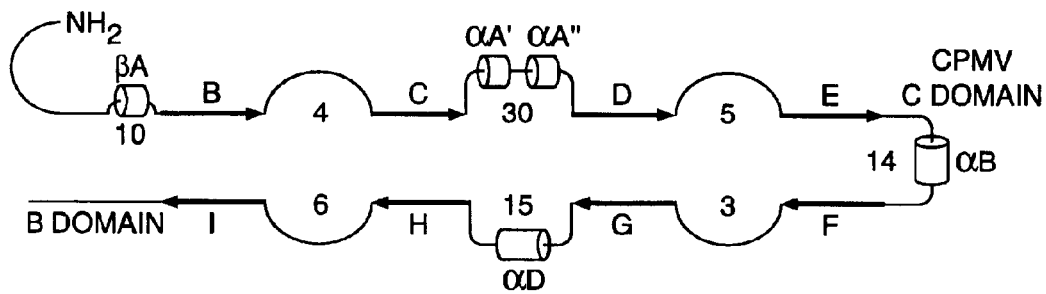
Figure 10C:
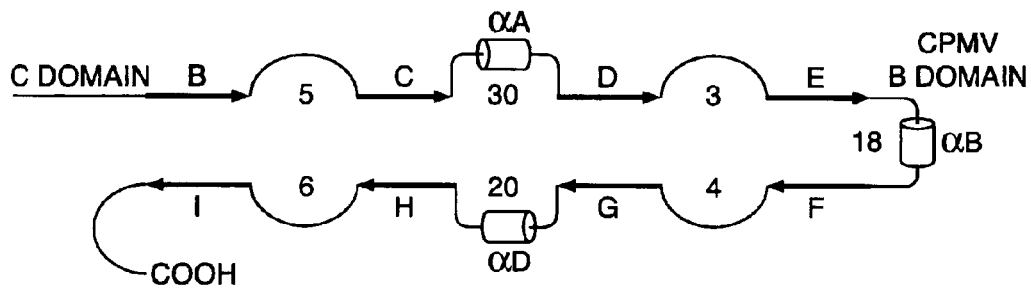
Figure 10G:
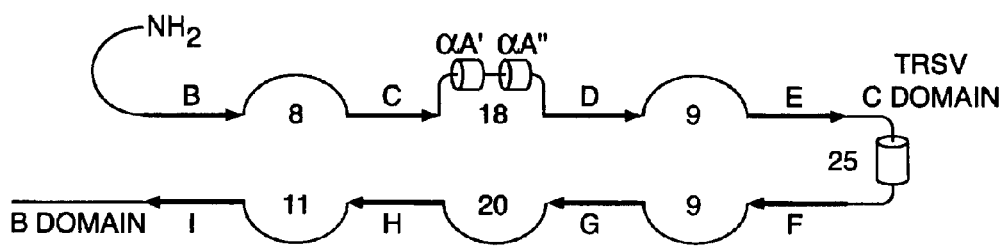
Figure 10H:
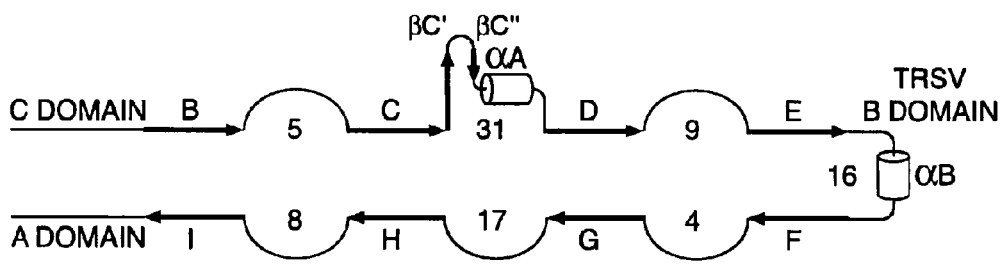
Figure 10I:
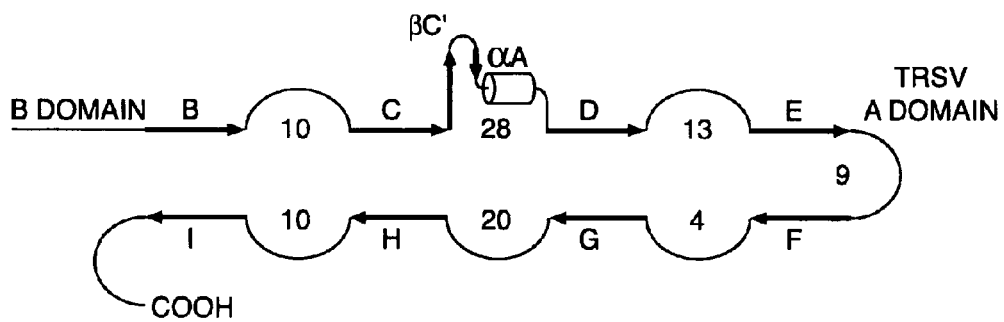
Figure 10J:
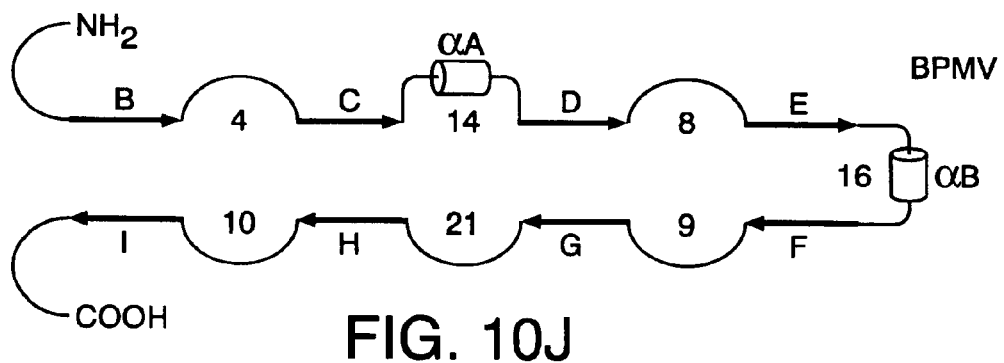
Figure 10K:
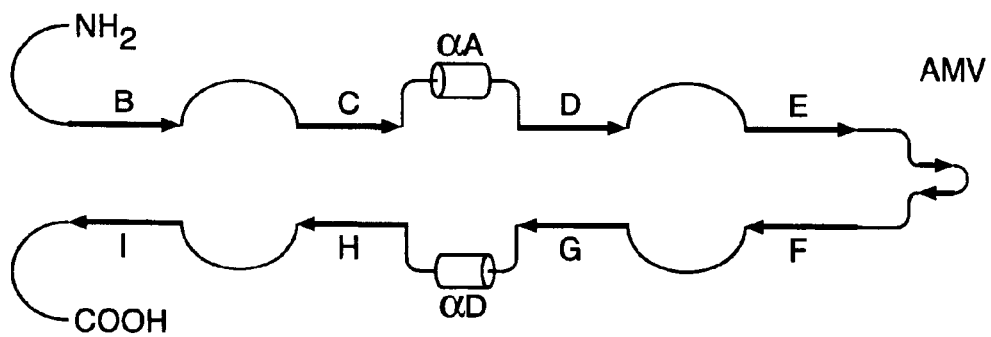
Figure 10L:
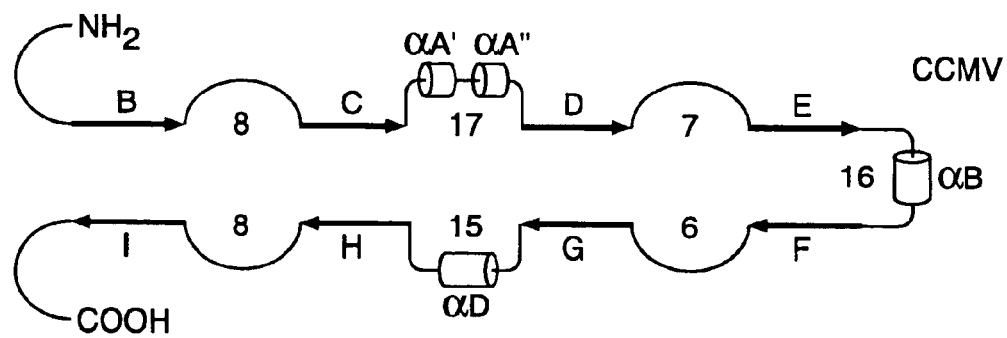
Figure 10M:
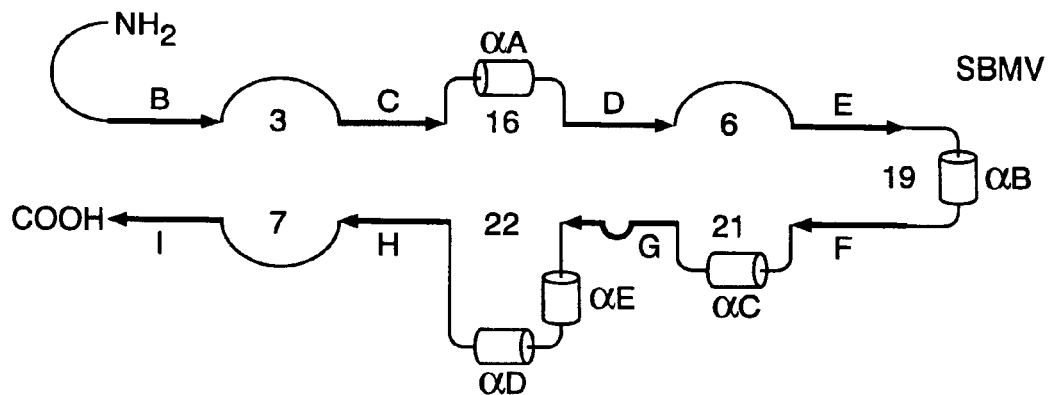
Figure 10N:
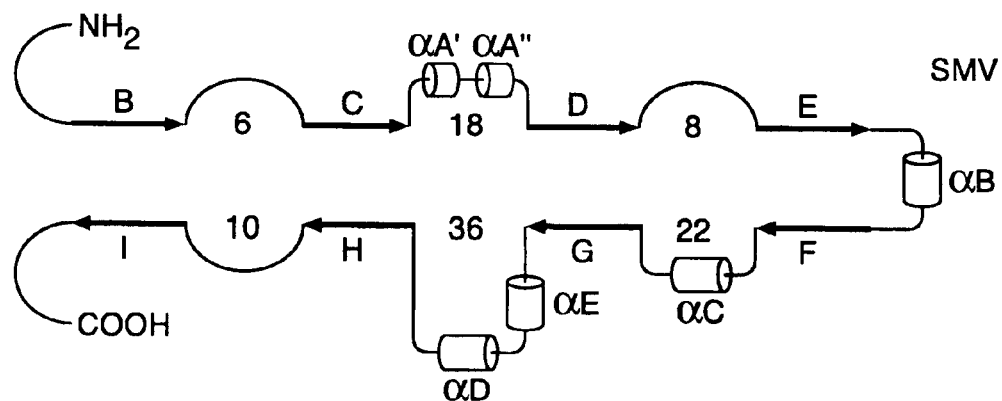
Figure 10O:
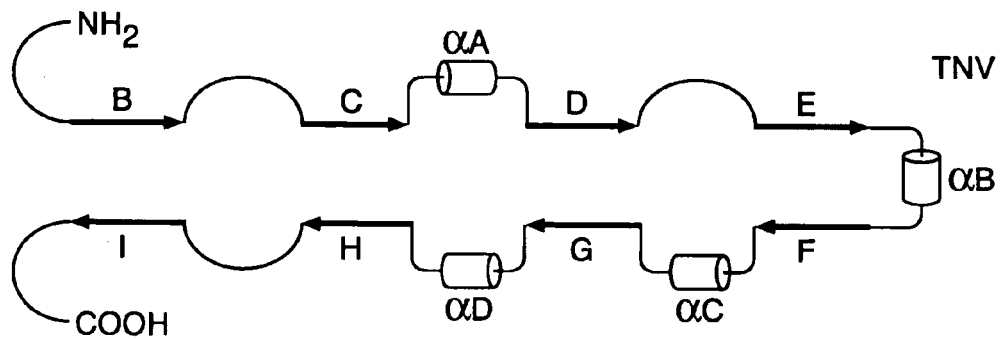
Figure 10P:
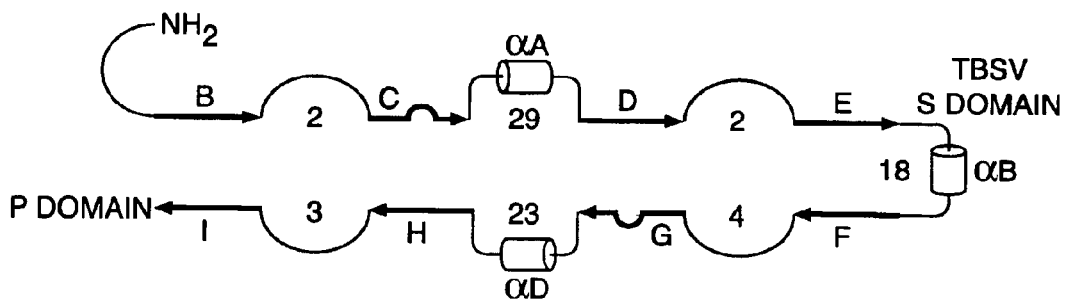
Figure 10Q:
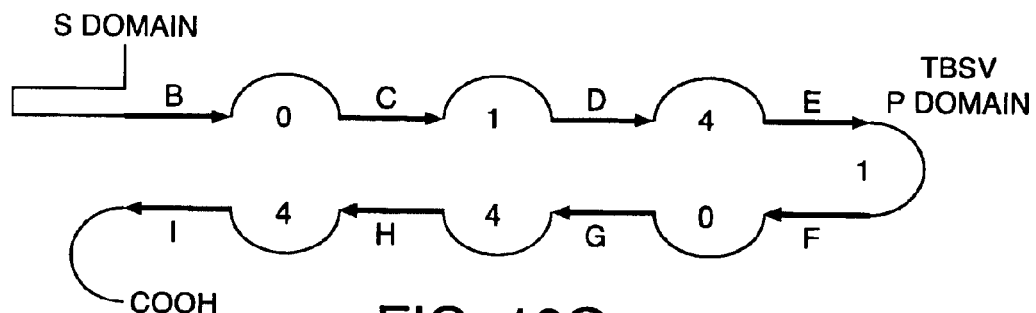
Figure 10R:
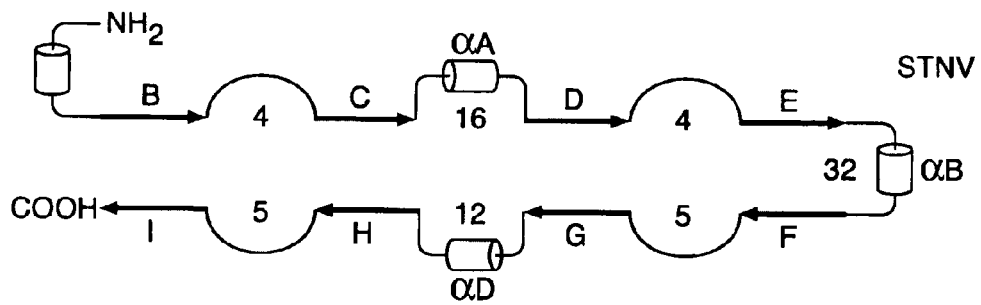
Figure 10S:
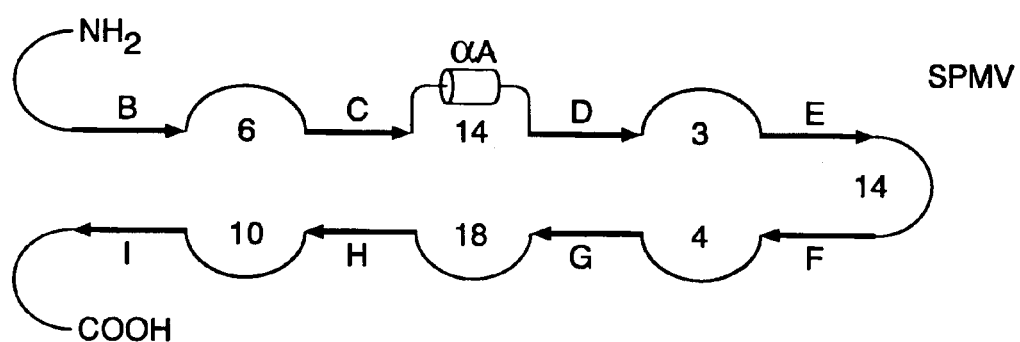
Figure 10T:
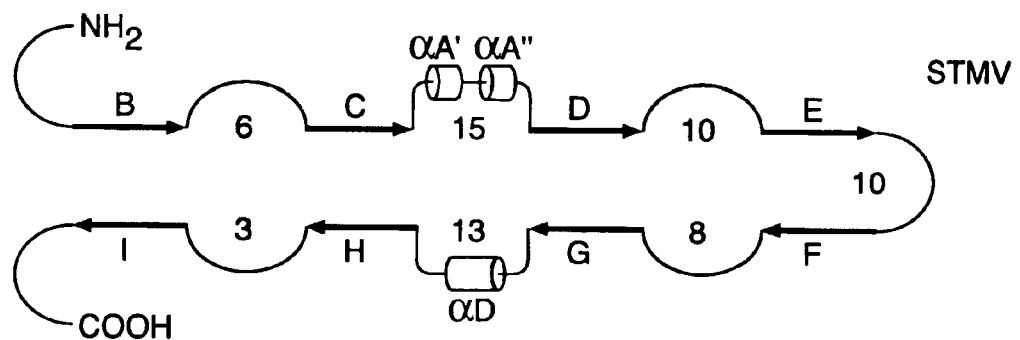
Figure 15:
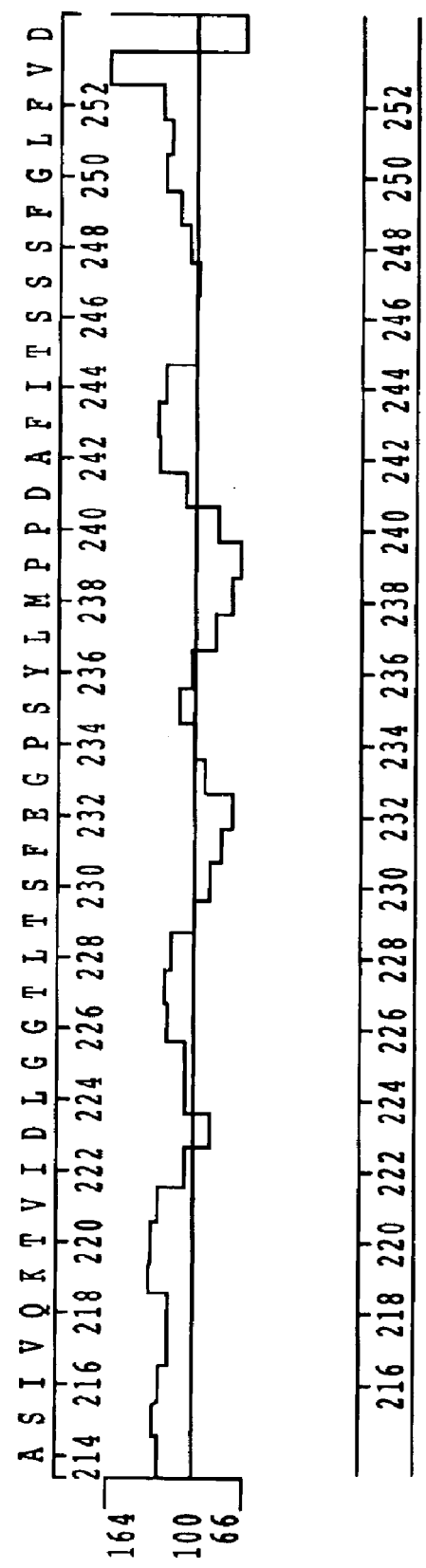
FIG. 15 illustrates a Chou-Fasman β-region prediction plot of RCNMV residues 214–257 using an algorithm based upon the structures found in 64 proteins.

FIG. 9 shows that neutralising antibody was produced in mice immunised with CPMV-HIV-I with a 50% neutralizing titre of about $\frac{1}{1000}$ in 83% of the mice. Antiserum diluted $\frac{1}{100}$ gave a mean neutralisation titre of 97% with 100% mice responding. The response was highly uniform. FIG. 9 also shows that a control group injected in parallel with wild type CPMV also gave a neutralizing response to HIV-I. The neutralisation titre was about 10-fold lower than with CPMV-HIV-I with a 50% neutralization titre of about $\frac{1}{100}$. This was evidently a de novo antibody response as there was no significant neutralization with serum from non-immunized litter mates even at a dilution of $\frac{1}{10}$.

The stability of the neutralizing antibody response to the CPMV-HIV chimaera was investigated by bleeding the mice again at 48 days after the second injection. These antisera had no significant neutralizing titre at a dilution of $\frac{1}{10}$, indicating that the level of neutralizing antibody had declined by over 100-fold. The neutralizing activity stimulated by wild type CPMV was now also undetectable.

The same mice were given a third injection of CPMV-HIV-I as before, 3 months after the second injection, and bled 14 days later. The mean neutralization titre was 54% at a $\frac{1}{1000}$ dilution with all mice now responding. There was no neutralization at this dilution with serum from mice boosted with wild type CPMV. Thus there was little overall increase in neutralising activity. The stability of the neutralizing antibody response to CPMV-HIV-I was checked with antiserum obtained after 56 days. The titres had fallen but anitsera from all mice still gave significant neutralization at a dilution of $\frac{1}{10}$, with a mean value of 58%. Neutralization by antisera from controls inoculated with wild-type CPMV was barely significant.

Neutralization of the homologous HIV-1 strain by antiserum obtained after the third injection was compared with the neutralization of HIV-1 strains RF and SF2. At a dilution at which strain IIIB was neutralized by 92%, RF was neutralized by 78%, and SF2 by 66%. Antisera made against wild type CPMV also neutralised all three strains, but relative to strain IIIB these antisera neutralised RF and SF2 less than antisera raised against CPMV-HIV-I.

It was confirmed that the neutralising antibodies in the antiserum made against the wild type CPMV were all specific for CPMV epitopes, with none made against the HIV-1 gp41 peptide, by antisera with purified wild type CPMV. Three successive adsorptions with CPMV did not significantly reduce the HIV-I neutralizing titre of the anti-CPMV-HIV-1 serum but reduced the neutralising titre of the anti-CPMV serum 5-fold. Thus we conclude that the majority of neutralising antibodies made against the CPMV-HIV chimaera were made against HIV-specific epitopes, but that CPMV stimulates antibodies that cross-react with neutralising epitopes of HIV-I.

EXAMPLE 6

Construction of cDNA Clones of CPMV RNA M and B which can be used to Directly Inoculate Plants cDNA clones of RNAs M and B of CPMV were constructed in pUC18 such that the 5' ends of the viral RNAs are abutted directly to the transcriptional start site of the CaMV 35S promotor. In addition, the RNA B clone (PCP1) can be linearised precisely at the 3' end of the viral sequence by restriction enzyme digestion at a unique MluI site and the RNA M clone (pCP2) can be treated similarly with EcoRI. Therefore, after digestion with these enzymes, run-off transcripts can be treated which contain no non-viral sequences at either their 5' or 3' ends.

The clones were constructed as described in Dessens, et al. [Journal of General Virology (1993) 73, 889–892]. The CaMV 35S promotor was cloned between the HindIII and PstI sites of pUC18, during which process the HindIII site was lost. This promotor sequence is flanked by SstII and StuI restriction sites, the latter of which allows blunt-end digestion to expose the transcriptional start site. cDNAs were generated for RNAs M and B and the 5' halves of these were cloned independently by digestion with SstI and BamHI respectively and ligation into a StuI/SstI or StuI/BamHI-cut CaMV 35S vector. The 3' halves of the RNAs were cloned into these constructs by utilising previously constructed cDNA clones (pMT7-601 and pBT7-123) which had been engineered such that the 3' ends could be precisely exposed by restriction enzyme digestion. RNA M was cloned on a PstI/EcoRI fragment and RNA B on a BglII/EcoRI fragment.

The CaMV 35S promotor utilises host plant DNA-dependent RNA polymerases and is highly active. Therefore an infection can be generated in the plant host simply by abrading the surface of the primary leaves in the presence of a mixture of linearised pCP1 and pCP2. The host polymerase directs transcription of viral RNA from the CaMV 35S promotor in vivo, and in cells where both pCP1 and pCP2 are transcribed, an infection similar to that obtained with wild type CPMV is generated. Therefore an in vitro RNA transcription step is no longer required. This represents a considerable advantage over the previous method for inoculating plants both in terms of ease of use and cost.

In order to allow the production of assembled particles of CPMV containing a foreign peptide which has been inserted immediately preceding the Pro$^{23}$ residue in the βB–βC loop of the small capsid protein, and in which the corresponding foreign nucleic acid has been inserted into the CPMV genome in the absence of direct sequence repeats flanking the insert and as an addition to the existing nucleic acid, cDNA clone pCP2 was mutated as described for pMT7 earlier in this specification to create a unique AatII site at position 2735 of the RNA M sequence. This was designated pCP2-AatII.

Oligonucleotide sequences encoding various foreign peptides (see Table 2) were substituted for the sequence between the Nhe1 and AatII sites of pCP2-AatII as described in Example 1. The pCP2-AatII variants and pCP-1 were linearised and inoculated onto the primary leaves of cowpea plants. In all cases infections developed and stable chimaeric virus particles expressing the appropriate foreign peptide were recovered from plants.

The following Examples illustrate the application of the present invention to plant viruses other than CPMV. The foreign peptide inserted in the coat protein of the assembled plant virus in question is the MUC1(16) epitope. The MUC1(16) epitope is a 16-mer peptide "GVTSAPDTRPA-PGSTA" SEQ ID NO:46 derived from the extracellular domain, tandem repeat sequence of human polythropine epithelial cell mucin (PEM) [for a review, see Apostolopoulos, V. and McKenzie, I. F. C. (1994) Crit. Rev. Immunol., 14, pp.293–309].

EXAMPLE 7

Inspection of the crystal structure of Southern bean mosaic virus (SBMV) strain C reveals that a portion of the loop between the αH and αI strands is well exposed upon the surface of the virus at the five-fold and quasi-six fold axes. This portion of the loop comprises amino-acids 251 to 255 of the linear coat protein sequence and nucleotides 3967 to 3981 of the genomic RNA sequence.

The cDNA of the complete 4194 bp RNA genome of SBMV is cloned into a derivative of pBluescript II plasmid vector lacking the T7 and T3 promoters using standard molecular biological techniques. The cDNA is cloned immediately downstream of a bacteriophage T7 such that a unique restriction enzyme site is present at the 3' terminus of the cDNA, thus allowing linearisation of the recombinant plasmid to generate run-off transcripts which mimic the wild-type RNA. As an alternative, the cauliflower mosaic virus (CaMV) 35S promoter may be used.

A sub-clone is then made from this full-length cDNA clone by inserting the BglII to XmnI fragment (genomic RNA nucleotides 3165 to 4161), which contains within it the whole coat protein open reading frame, into BamHI/HincII digested pBluescript II. This sub-clone is further manipulated via site-directed mutagenesis at genomic nucleotide positions 3969 (change A to C) and 3984 (G to T) to create BamHI and HpaI restriction sites, respectively.

The modified subclone is digested with these enzymes and separated from the small excised fragment which is replaced by oligonucleotides coding for the excised nucleotide sequence plus nucleotides coding for an epitope sequence MUC1(16). The following five constructs contain the inserted peptide sequence either between coat protein amino-acids 251 and 252, or 252 and 253, or 253 and 254, or 254 and 255, or 255 and 256 (see FIG. 11).

The modified region of the coat protein from each of these constructs is isolated on a HindIII/AvrII fragment (genomic nucleotides 3434 to 4096) and used to replace the corresponding fragment in the full-length cDNA clone of the virus. Each of these clones is then linearised at the 3' terminus of the cDNA and, in the case of a T7 bacteriophage promoter construct, used to generate capped run-off RNA transcripts which are then inoculated onto the host-plant (Vigna unguiculata), or inoculated directly when under the control of the 35S promoter.

The inoculated plants are monitored for symptoms, and the strength of symptoms, yield and stability for each construct are assessed in order to determine the optimal insertion site. If desirable, purified virus may also be used to immunise experimental animals in order to determine the levels of immune response generated by each construct.

This Example can be adapted to allow insertion in any of the exposed loops of SBMV. Similarly, any peptide epitope sequence can be used instead of MUC1(16).

EXAMPLE 8

This example describes the determination of an insertion site for epitopes by alignment of the primary sequence of a virus whose structure is unknown (lucerne transient streak virus, LTSV), against those of viruses whose structure has been determined.

The crystal structures of two sobemoviruses, SBMV and Sesbania mosaic virus (SMV), have been solved at high resolution. Comparison of the crystal structures reveals that all the secondary structural elements are well conserved between the viruses and, in particular, the protruding loop between the βH and βI is almost identical in shape and location between the two viruses. This structural element would therefore be expected to be well conserved in all sobemoviruses.

Alignment of the primary sequences of LTSV, SBMV and SMV shows a strong conservation of residues between the three viruses within the βH strand region and significant sequence homology within the βI strand (see FIG. 12). This allows the loop region of LTSV to be inferred as spanning amino acids 218 to 224 of the coat protein.

The 4.275 kb RNA genome is cloned as cDNA, as described for SBMV in Example 7. The genomic clone is then modified by site directed mutagenesis at position 3959 (C to T) and position 3998 (T to C) to create unique PstI and KpnI restriction enzyme sites, respectively. The modified genomic clone is digested with these restriction enzymes and separated from the small excised fragment which is replaced by oligonucleotides coding for the excised nucleotide sequence plus nucleotides coding for the epitope sequence MUC1(16). The following six constructs contain the epitope sequence either between coat protein amino acids 218 and 219, or 219 and 220, or 220 and 221, or 221 and 222, or 221 and 223, or 223 and 224 (see Each of these clones is linearised at the 3' terminus of the cDNA and, in the case of a T7 bacteriophage promoter construct, used to generate capped run-off RNA transcripts which are then inoculated onto the host-plant (Nicotiana clevelandii), or inoculated directly when under the control of the 35S promoter.

The inoculated plants are monitored for symptoms, and the strength of symptoms, yield and stability for each construct are assessed in order to determine the optimal insertion site. If desirable, purified virus may also be used to immunise experimental animals in order to determine the levels of immune response generated by each construct.

This Example can be adapted to allow insertions in any of the exposed loops of LTSV. Similarly, any peptide epitope sequence can be used instead of MUC1(16).

EXAMPLE 9

This example describes the determination of epitope insertion sites in a virus (red clover necrotic mosaic virus, RCNMV) whose coat-protein morphology is known to be similar to a second virus (tomato bushy stunt virus, TBSV) belonging to a different virus family whose crystal structure has been solved. In this case, there is only minimal homology between the two coat protein primary sequences, hence secondary structure prediction algorithms are used to assist in the assignment of a particular loop region.

The crystal structure of the coat protein of TBSV reveals that each of the 180 coat protein subunits forming the T=3 icosahedron consists of two β-barrel domains. The first domain forms the surface of the virus particle and is termed the S domain and is equivalent to the single domain found in SBMV. The second, much smaller, domain forms a surface protrusion at right angles to the plane of the S domain. This P domain forms dimeric interactions with the P domain of a neighbouring coat-protein subunits at the strict and quasi two-fold axes of the icosahedron. The presence of the P domain causes the virions to appear distinctly granular when examined under the electron microscope. Between the S and P domains is a short flexible linker followed by a pair of β-strands connected by a loop which appears to be highly exposed on the viral surface with no obvious role in the contacts between subunits. This loop provides a target for epitope insertions.

Dianthoviruses (e.g. RCNMV) also appear distinctly granular when subjected to electron microscopy, and this together with the size of the coat proteins and their limited homology with those of tombusviruses suggests that they may have structural similarity. Alignment of the coat protein sequences of RCNMV and TBSV (see FIG. 14) using a Lipman-Pearson alignment algorithm, which recognises sequence conservation as well as identity, gives a similarity index of 26.9 (strict homology is 23%). From the alignment it can be seen that the S domain is better conserved (TBSV residues 100 to 269, strict homology 36%) than the P domain (TBSV residues 270–388) which is poorly conserved.

The loop of interest comprises TBSV residues $L^{280}$ $A^{281}$ $G^{232}$ and the sequence around this region shows some conservation in RCNMV, however secondary structure prediction algorithms are also used to predict the location of β-strands and hence the loops which lie between them. FIG. 15 shows a Chou-Fasman β-region prediction plot of RCNMV residues 214–257 using an algorithm based upon the structures found in 64 proteins. This type of plot is claimed to be 80% accurate at predicting beta strands of interest The plot suggests that beta strands of interest are located between residues 214–221 and 226–228, hence the loop at the tip of the domain will be residues 222–225 and residues 245–248. A more sophisticated prediction algorithm, the EMBL PHDsec program based upon trained neural networks, may also be used. The resulting output for the region of interest is shown in FIG. 16. This locates the β-strands to residues 220–223 and 227–239, therefore the loop is comprised of residues 224–226. Combining the two sets of data, the loop will lie within the region spanned by residues 222 to 226.

Dianthoviruses have a bipartite RNA genome, both RNAs being required for infectivity. Accordingly, RCNMV RNAs 1 and 2 are cloned as cDNA, using standard molecular biological techniques, into a suitable vector, downstream of a CaMV 35S promoter. As an alternative, the T7 promoter may be used. Both clones are engineered such that they can be linearised at the 3' termini of the cDNAs.

The cDNA genomic clone of RNA1 is modified by site directed mutagenesis at positions 3078 (A to G) and 3081 (G to C), to create a unique ApaLI restriction site, and at positions 3108 to 3111 (ACTC to GTTA) to create a unique HpaI restriction site. The mutation at position 3081 is not silent, however the correct codon is restored when ligating in oligonucleotides to generate the epitope insertion. The modified genomic clone is digested with these restriction enzymes and separated from the small excised fragment which is replaced by oligonucleotides coding for the excised nucleotide sequence plus nucleotides coding for the epitope sequence MUC1(16). The following six constructs, contain the epitope sequence either between coat protein amino acids 221 and 222, or 222 and 223, or 223 and 224, or 224 and 225, or 225 and 226, or 227 (see FIG. 17).

Each of these clones is linearised at the 3' terminus of the cDNA and, in the case of a T7 bacteriophage promoter construct, used to generate capped run-off RNA transcripts. These are then mixed with similar transcripts from the linearised cDNA clone of genomic RNA2 and inoculated onto the host-plant (*Nicotiana clevelandii*). Linearised clones are inoculated directly when under the control of the CaMV 35S promoter.

The inoculated plants are monitored for symptoms, and the strength of symptoms, yield and stability for each construct are assessed in order to determine the optimal insertion site. Purified virus may also be used to immunise experimental animals in order to determine the levels of immune response generated by each construct.

This Example can be adapted to allow insertions in any exposed loops of RCNMV. Similarly, any peptide epitope sequence can be used instead of MUC1(16).

The following Examples demonstrate application of the present invention to non-icosahedral plant viruses.

EXAMPLE 10

Tobacco Mosaic Virus

Tobacco mosaic virus (TMV) is a member of the tobamovirus genus of plant viruses whose particle structure is that of a rigid rod 300 nm long and 18 nm in diameter with a central hole of 4 nm. The rod is formed by 2100 coat protein subunits arranged in a right-handed helix with a pitch of 2.3 nm and 16.33 subunits per turn which encapsidate the viral RNA of 6.5 Kb The structure of the individual coat protein subunits of this virus has been solved at atomic resolution and consists of a core made up of a right-handed, four anti-parallel α-helix bundle with left and right slewed helices (LS & RS) and left and right radial helices (LR & RR) extending outwards from an RNA binding site (Namba, et al. 1989). The crystal structure suggests that possible insertion sites for peptides or polypeptides could be at or close to the termini (both N- and C-) and in the loop connecting the RS and RR helices. In fact, expression systems have been developed which exploit two of these potential sites.

Early work on direct fusions to the C-terminus demonstrated that whilst some short additional sequences were allowed (7 amino-acids) others prevented virus assembly and movement through the plant (Takamatsu, et al. 1990). However it was subsequently found that C-terminal extensions of TMV could be exploited as an efficient expression system provided that mechanisms to allow for the production of unmodified coat protein as well as extended coat protein were employed. It has been demonstrated that direct fusions to the C-terminus can be achieved by utilizing the phenomenon of stop codon read-through (Hamamoto, et al. 1993; Sugiyama, et al. 1995; Turpin, et al. 1995) whereby approximately 5% of the coat protein subunits possess C-terminal extensions. A second method for generating a mixture of wild-type coat protein and modified coat protein is to inoculate plants with a mixture of two viruses, one being a complete virus genome containing a modified coat protein and the second being a virus lacking the movement protein but containing an unmodified coat protein (Beachy, et al. 1996). It has also been shown that viruses with additions to the C-termini of all the coat protein subunits can assemble and move systemically in infected plants and are stable over multiple passages, however in this case the additional sequences are not fused directly to the C-terminus of the coat protein, but are inserted at a site 5 or 6 amino acids from the C-terminus (Fitchen, et al. 1995; Beachy, et al. 1996).

Short peptides (4 or 12 amino-acids) have also been inserted in the loop connecting the RS and RR helices, between coat protein amino-acids 63 and 66 accompanied by a deletion of amino-acids 64 and 65 (Turpen, et al. 1995). These modified viruses assemble and systemically infect inoculated plants and can be recovered with high yields.

EXAMPLE 11

Potato Virus X

Potato virus X (PVX) is a member of the potexvirus genus of plant viruses whose particle structure is that of a flexuous rod 515 nm long and 13 nm in diameter with a central hole of 1.7 nm. The rod is formed by 1270 coat protein subunits arranged in a right handed helix with a pitch of 3.4 nm and 8.875 subunits per turn which encapsidate the viral RNA of 6.4 kb. A model of the structure of PVX has been proposed based upon tritium planigraphy and immunological analysis (Baratova, et al. 1992a, 1992b) where the N-terminus of the coat protein is exposed between amino-acid residues 1–33 and forms a beta sheet composed of three beta strands. In contrast to TMV, the C-terminus is not exposed and it is thought to lie underneath the surface structure formed by the N-terminus. Therefore, based upon this low resolution data, fusions of peptides and polypeptides to the N-terminus should be possible.

It has been demonstrated that polypeptides as large as 27 kDa can be fused to the N-terminus of the PVX coat protein (Santa-Cruz, et al. 1996), however, as was demonstrated for C-terminal fusions to TMV, it proved necessary to engineer the construct in such a way that a mixture of free coat protein and polypeptide/coat protein fusion was produced in order to allow virus assembly and spread within the plant. This was achieved by inserting a 16 amino-acid sequence between the final codon of the polypeptide and Pro$^4$ of the coat protein. This sequence codes for the core FMDV 2A protease which autocatalytically cleaves between its final amino-acid and the proceeding proline residue of the PVX coat protein, however this autocatalytic event occurs inefficiently such that the majority of protein produced is the fusion product with a smaller proportion of free polypeptide and coat protein, however the amount of free coat protein generated is sufficient to ensure efficient assembly and spread of virus particles which also carry the polypeptide-coat protein fusion.

EXAMPLE 12

Preparation of PVX-MAST8

In order to utilise linearised DNA for the inoculation of plants, the full length viral cDNA from pTXS.L2a-CP (patent application No. 9420989.7) was transferred into plasmid pCP8 such that the viral cDNA was fused directly to the transcriptional start site of the CaMV 35S promoter. This plasmid was called pTXS6. Following the insertion of peptides, as described below, the DNA was linearised with SpeI and used to inoculate young *Nicotiana benthamiana* leaves in order to produce viral particles (Brennan et al, 1999).

Plasmid pTXS6 was digested with NheI and AflII and five oligonucleotides coding for the excised regions of the PVX vector, an initiating methionine and amino acids 1–38 (GQNNGNQSFEEDTEKDKPKYEQGGIIDIDF) SEQ ID NO: 121 from the D2 peptide derived from an *S. aureus* fibronectin binding protein (FnBP) were inserted (as illustrated below). This plasmid, termed pTXS6-MAST8, therefore contained the coding sequence for amino acids 1–38 in frame and directly in front of the 16aa sequence coding for the core FMDV 2A protease.

```
     NheI,ATG,    D2peptide,                        AflII
      CTAGCATG......................................AATTTTGACCTTC    SEQ ID NO:122
          GTAC......................................TTAAAACTGGAAGAATT SEQ ID NO:123
```

The DNA was linearised and used to inoculate *Nicotiana benthamiana* using 0.5 µg of linear DNA per leaf. After 14 days, the leaves were harvested and virus particles extracted by homogenisation in 50 mM sodium borate pH 9, 10 mM β-mercaptoethanol. Following three chloroform extractions, the virus particles were precipitated once with 5% (w/v) PEG 8000 and three times with 5% PEG 8000, 0.25M NaCl. The final pellet was resuspended in 50 mM sodium borate pH 9, 20% glycerol and stored at −70° C. The final concentation and quality of these viral particles, termed PVX-MAST8, was determined by comparison with PVX standards purified using standard protocols on SDS PAGE gels. From this it was determined that approximately 10% of the viral coat protein subunits carried the peptide fusion.

Mice were immunised subcutaneously with PVX-MAST8 in adjuvent and high titres of FnBP-specific antibody were obtained. This sera was shown to completely inhibit the binding of fibronectin to immobilised recombinant FnBP.

This study demonstrates that the D2 peptide is highly immunogenic when expressed on the surface of PVX and that the viral particles can be purified from plant sap.

EXAMPLE 13

Preparation of pTXS2-ATZ27

A number of proteins have been expressed on the surface of PVX using the original pTXS.L2a-CP vector described above. A single-chain antibody fragment against the triazine herbicide atrazine was amplified by PCR, digested with ClaI and AflII and ligated into pTXS.L2a-CP digested with the same enzymes. Following sequence analysis to confirm that the scFv was in frame with the 2A protease of FMDV and the viral coat protein, the plasmid DNA (pTXS2-ATZ27) was linearised with SphI and infectious transcripts produced using standard protocols. The infectious transcripts were then used to inoculate *Nicotiana benthamiana* plants.

Fourteen days after inoculation, total soluble protein was extracted from a systemically infected leaf and analysed by western blot analysis, using antisera raised against the coat protein of PVX. Both the viral fusion protein of 53 kDa and the cleaved viral coat protein of 24.8 kDa were clearly detected. The number of viral coat protein subunits carrying the peptide fusion ranged from 5–50% in different plants.

In order to confirm affinty for atrazine, ELISAs were carried out using atrazine-BSA coated plates. Plant sap was extracted from systemically infected leaves, using 1×PBS buffer and the amount of total soluble protein estimated using a BIO-RAD protein assay. Total soluble protein at 50–0.1 mg/ml was then added to the ELISA plate. In a similar manner, the amount of PVX in each sample was estimated and plant extracts containing 50–0.1 mg/ml of PVX were added to the ELISA plate. In each case the viral fusion protein was then detected with an anti-PVX polyclonal antisera. Affinity for the atrazine was clearly demonstrated in those samples expressing the viral fusion protein compared with wild type PVX infected or non-infected plant tissue. In each case an increase in relative affinity correlated with an increase in the amount of viral coat protein subunits carrying the peptide fusion.

EXAMPLE 14

Plum Pox Virus

Plum Pox virus (PPV) is a member of the potyvirus genus of plant viruses (family potyviridae) whose particle structure is that of a flexuous rod 750 nm long and 11–13 nm in diameter. The rod is formed by more than 2000 coat protein subunits arranged in a right handed helix with a pitch of 3.4 nm which encapsidate the viral RNA of 9.8 kb. Very little structural information is known about potyviruses, however immunological and protease treatment studies have shown that both the N- and C-termini are surface exposed (Shukla, et al. 1988; Shukla and Ward, 1989) and might therefore be useful sites for the insertion of peptides or polypeptides. In addition there are naturally occurring mutants of PPV which are non-aphid transmissible which have a deletion of 15 amino-acids within the N-terminus of the coat protein (NAT mutants: Maiss, et al. 1989) which includes the Gly of the Asp-Ala-Gly amino-acid triad essential for aphid transmission (Atreya, et al. 1990 and 1991). Therefore PPV is naturally capable of possessing at least an extra 15 amino-acids within its N-terminus and the site of the naturally occurring deletion is a logical place to insert peptides or polypeptides. In addition, the length of the N-terminus is highly variable between potyviruses, suggesting that potyviruses will tolerate different sequence lengths, and this region of the coat protein is known to be highly immunogenic.

Insertions of 15 and 30 amino-acids have been made within the N-terminus as described above (Fernandez-Fernandez et al. 1998). The chimaeric viruses were infectious, genetically stable and accumulated in the infected plants to wt levels and gave similar yields on purification. In contrast to some of the TMV systems and the PVX system, additions to all the coat protein subunits were tolerated.

EXAMPLE 15

Tobacco Rattle Virus

Tobacco rattle virus (TRV) is a member of the tobravirus genus of plant viruses whose particle structure is that of a rigid rod. TRV has two genome components which are encapsidated separately into rods of about 190 nm in length and 50 to 115 nm in length depending upon the isolate. The rods are 23 nm in diameter with a central hole of 5 nm. The coat protein subunits are arranged in a right handed helix with a pitch of 2.5 nm and the number of subunits per turn has been estimated at either 25.33 or 32.33. The longer particle encapsidates genomic RNA1 which is 6.8 kb in length and the shorter particle encapsidates RNA2 which ranges in size from 1.8 kb to 4.5 kb depending upon the isolate. RNA1 is capable of independent replication and systemic spread in infected plants, however no virus particles are formed in these infections since the coat protein gene is carried on RNA2 and transmission is difficult Infections containing both RNA1 and RNA2 produce virus particles and are readily transmissible between plants by mechanical inoculation and nematodes.

No detailed structural information is known for TRV, however coat protein sequence alignments of tobraviruses with those of tobamoviruses suggest that they share a common evolutionary origin (Goulden, et al. 1992) and may therefore have very similar structures. Immunological and proteolytic analysis of the tobraviral particle shows that the C-terminus is exposed upon the viral surface and can be removed without affecting particle integrity (Legorburu, et al. 1996) and it has also been shown by NMR spectroscopy that the C-terminus is highly mobile (Mayo, et al 1993). Therefore, as is the case with TMV, the C-terminus of TRV may be a suitable site for the insertion of peptides and polypeptides.

Although TRV and TMV are thought to be structurally very similar, there may be advantages in using the former in preference to the latter for the expression of peptides and polypeptides as follows:
1. TRV does not require coat protein to systemically invade host plants, therefore additions to the C-terminus will not interfere with virus spread.
2. The C-terminus is much longer than that of TMV and is not required for particle stability, and may therefore be replaced by foreign sequences. Replacement is less likely to interfere with virus assembly than addition.
3. The C-terminus is highly mobile and this flexibility may allow the addition of foreign sequences without interfering with viral assembly.

The cDNA of the complete 6791 b RNA1 of TRV strain PSG is synthesized and cloned into a derivative of a pBluescript II SK+ vector (lacking the T7 and T3 promoters) using standard molecular biological techniques. The cDNA is cloned such that the 5' end is at the transcriptional start of a bacteriophage T7 promoter and the 3' end can be exposed by linearisation with a unique restriction enzyme site in order to generate run-off transcripts which mimic the wild-type RNA sequence. As an alternative, the cauliflower mosaic virus (CaMV) 35S promoter is used. The cDNA of the complete 1905 b RNA2 of TRV strain PSG is synthesized and cloned in a similar fashion. Infections are generated in host plants (Nicotiana clevelandii) by linearising the RNA1 and RNA2 clones at their 3' termini and either inoculating with a mixture of run-off transcripts in the case of T7 controlled clones or mixing and inoculating the plasmid DNA directly in the case of 35S controlled clones.

The requirement for C-terminal sequences of the coat protein for assembly is then investigated by stepwise deletions introduced into the coat protein gene on the RNA2 cDNA clone, utilising naturally occurring unique Sal I and PpuM I restriction enzyme sites at RNA2 positions 1125 and 1224 respectively (Note : Sal I is present in the polylinker of p Bluescript II, but is removed during the cloning of the cDNA of RNA2). The RNA2 clone is digested with Sal I and PpuM I and separated from the 100 bp excised fragment which is replaced by oligonucleotides containing increasingly long deletions of the coat protein C-terminus. Five constructs are made containing deletions of 5, 10, 15 , 20 and 22 amino-acids (FIG. 18). These constructs and the unmodified clone are inoculated onto plants (as described above) and monitored for symptom development. Sap extracts from infected leaves are then examined under the electron microscope for the presence of viral particles and, where particles are present, purifications are done to assess yield.

The largest coat protein deletion which allows particle assembly comparable to undeleted TRV is then selected as a potential carrier for peptides and polypeptides. Hence, overlapping oligonucleotides are assembled containing the sequence corresponding to this deletion plus the coding sequence of choice for a peptide or polypeptide to be inserted between the ultimate amino-acid of the deletion and the stop codon. This construct is inoculated onto plants as described above and the strength of symptoms, virion assembly, yield and stability of the construct is assessed. In the event that particle assembly is prevented by the addition of the non-native sequences then additional constructs are made containing smaller deletions of the C-terminus of the coat protein.

Purified virus from successful constructs may further be used to immunise experimental animals to determine the strength of the immune response generated by the inserted, non-native sequences.

TABLE 2

Foreign peptide sequences expresssed as chimaeric virus particles produced by direct inoculation of plants with cDNA clones.

| CONSTRUCT | LENGTH (amino acids) | PEPTIDE SOURCE |
| --- | --- | --- |
| HIV-1 | 22 | amino acids 732–752 of gp41 of HIV-I strain IIB |
| HIV-3 | 6 | amino acids 312–317 of gp120 of HIV-I strain IIIB (the V3 loop) |
| HIV-4 | 11 | amino acids 140–150 of gp120 of HIV-I strain IIIB (the V1 loop) |
| HIV-5 | 11 | amino acids 117–127 of HIV-I strain IIIB |
| FMDV-5 | 19 | amino acids 141–159 of VP1 of FMDV strain $O_1$ (the G-H loop) |
| FMDV-12 | 21 | A peptide sequence form VP1 of FMDV strain CS8 (the G-H loop) |
| FMDV-13 | 23 | A peptide sequence from VP-1 of FMDV strain A10 (the G-H loop) |
| FMDV-14 | 10 | amino acids 40–49 of VP1 of FMSV strain $O_1$ (the B-C loop) |
| PARVO-1 | 17 | amino acids 13–29 of VP2 of canine parvovirus |
| PARVO-2 | 17 | the insert sequence of PARVO-1 in reverse |
| PARVO-3 | 17 | as flanking sequence variant of PARVO-1 |
| GNRH-1 | 10 | an immunodominant epitope form pig gonadotrophin releasing hormone |
| MAST-1 | 30 | derived from the fribronectin binding protein of *Staphylococcus aureus* |
| MAST-2 | 38 | a longer version of MAST-1 |
| HRV-2 | 14 | amino acids 85–98 of VP1 of HRV strain 14 |

REFERENCES

Atreya C. D., Raccah B. & Pirone T. P., 1990. A point mutation in the coat protein abolishes aphid transmissibilty of a potyvirus. *Virology* 178: 161–165.

Atreya P. L., Atreya C. D. & Pirone T. P., 1991. Aminoacid substitutions in the coat protein result in loss of insect transmissibility of a plant virus. *Proc. Natl. Acad. Sci. USA* 88: 7887–7891.

Baratova L. A., Grebenshchikov N. I., Shishkov A. V., Kashirin I. A., Radavsky Y. L. Jarvekulg L., & Saarma M., 1992(b). The topography of the surface of potato virus X: tritium planigraphy and immunological analysis. *J. Gen. Virol.* 73: 229–235.

Baratova L. A., Grebenshchikov N. I., Dobrov E. N., Gedrovich A. V., Kashirin I. A., Shishkov A. V., Efimov A. V., Jarvekulg L., Radavsky Y. L. & Saarma M., 1992(b). The organisation of potato virus X coat proteins in virus particles studied by tritium planigraphy and model building. *Virology* 188: 175–180.

Beachy R. N., Fitchen J. H. & Hein M. B., 1996. Use of plant viruses for delivery of vaccine epitopes In: *Engineering Plants for Commercial Products and Application. Annals of the New York Academy of Sciences Vol. 792.* Eds.: Collins G. B. & Shelford. New York Academy of Sciences USA.

Fernandez-Fernandez M. R., Martinez-Torrecuadrada J. L., Casal J. I. & Garcia J. A., 1998. Development of an antigen presentation system based on plum pox potyvirus. *FEBS Letters* 427: 229–235.

Fitchen J., Beachy R. N. & Hein M. B., 1995. Plant virus expressing hybrid coat protein with added murine epitope elicits autoantibody response. *Vaccine* 13: 1051–1057.

Goulden M. G., Davies J. W., Wood K. R. & Lomonossoff G. P., 1992. Structure of tobraviral particles: a model suggested from sequence conservation in tobraviral and tobamoviral coat proteins. *J. Mol. Biol.* 227: 1–8.

Hamamoto H., Sugiyama Y., Nakagawa N., Hashida E., Matsunaga Y., Takemoto S., Watanabe Y. & Okada Y., 1993. A new tobacco mosaic virus vector and its use for the systemic production of angiotensin-I-converting enzyme inhibitor in transgenic tobacco and tomato. *Bio/technology* 11: 930–932.

Legorburu F. J., Robinson D. J. & Torrance L., 1996. Features on the surface of tobacco rattle tobravirus particle that are antigenic and sensitive to proteolytic digestion. *J. Gen. Virol.* 77: 855–859.

Maiss E., Timpe U., Brisske A., Jelkmann W., Casper G., Himmler G., Mattanovich D. & Katinger H. W. D., 1989. The complete nucleotide sequence of plum pox virus RNA. *J. Gen. Virol.* 70: 513–524.

Mayo M. A., Brierly K. M. & Goodman B. A., 1993. Developments in the understanding of the particle structure of tobraviruses. *Biochimie* 75: 639–44.

Namba K., Pattanayek R. & Stubbs G., 1989. Visualisation of protein-nucleic acid interactions in a virus. Refined structure of intact tobacco mosaic virus at 2.9 angstrom resolution by X-ray fibre diffraction. *J. Mol. Biol.* 208: 307–325.

Santa-Cruz S., Chapman S., Roberts A. G., Roberts I. M., Prior D. A. M. & Oparka K. J., 1996. Assembly and movement of a plant virus carrying a green fluorescent protein overcoat. *Proc. Natl. Acad. Sci. USA* 93: 6286–6290.

Shukla D. D., Strike P. M., Tracy S. L., Gough K. H. & Ward C. W., 1988. The N and C termini of the coat proteins of Potyviruses are surface located and the N terminus contains the major virus specific epitopes. *J. Gen. Virol.* 69: 1497–1508.

Shukla D. D. & Ward C. W., 1989. Structure of potyvirus coat proteins and its application in the taxonomy of the potyvirus group. *Adv. Virus Res.* 36: 273–314.

Sugiyama Y., Hamamoto H., Takemoto S., Watanabe Y. & Okada Y., 1995. Systemic production of foreign on the particle surface of tobacco mosaic virus. *FEBS Letters* 359: 247–250

Takamatsu N., Watanabe Y., Yanagi H., Meshi T., Shiba T. & Okada Y., 1990. Production of enkephalin in tobacco protoplasts using tobacco mosaic virus RNA vector. *FEBS Letters* 269: 73–76

Turpen T. H., Reini S. J., Charoenvit Y., Hoffman S. L., Fallarme V. & Grill L. K., 1995. Malarial epitopes expressed on the surface of recombinant tobacco mosaic virus. *Bio/technology* 13: 53–57.

What is claimed is:

1. A method for producing plant virus particles comprising: a) providing i) a plant virus genome comprising nucleic acid which codes for a coat protein, ii) a foreign nucleotide sequence coding for a portion of a mammalian viral protein, wherein said portion is between six and twenty-one amino acids in length; b) modifying said plant virus genome by inserting said foreign nucleotide sequence coding for a foreign peptide at a site within said nucleic acid which codes for the coat protein so as to create a modified plant virus genome comprising an insert, wherein said site is free from direct sequence repeats flanking said insert; c) infecting plant material selected from the group consisting of plants, plant tissue, plant cells and protoplasts with said modified plant virus genome to produce assembled particles of a modified virus; and d) harvesting assembled particles of the modified virus from said plant material.

2. The method according to claim 1, in which the insert is an addition to said coat protein.

3. The method according to claim 1, in which the foreign nucleotide sequence is inserted by i) selecting two different restriction enzyme sites in the plant viral nucleic acid; ii) cutting the plant viral nucleic acid using the corresponding restriction enzymes; and iii) inserting into the cut viral nucleic acid a pair of complementary oligonucleotides which encode the foreign peptide and which terminate in ends compatible with the restriction enzyme cutting sites.

4. A method according to claim 3, in which in the complementary oligonucleotides, the sequence encoding the foreign peptide is flanked by plant virus-specific sequences so that the foreign nucleotide sequence is inserted as an addition to the plant viral nucleic acid.

5. A method for producing plant virus particles comprising: a) providing i) a plant virus genome comprising nucleic acid which codes for a coat protein, ii) a foreign nucleotide sequence coding for a portion of a mammalian viral protein, wherein said portion is between six and twenty-one amino acids in length; b) modifying said plant virus genome by inserting said foreign nucleotide sequence coding for a foreign peptide at a site within said nucleic acid which codes for the coat protein so as to create a modified plant virus genome comprising an insert, wherein no coat protein coding sequences are deleted, and wherein said site is free from direct sequence repeats flanking said insert; c) infecting plant material selected from the group consisting of plants, plant tissue, plant cells and protoplasts with said modified plant virus genome to produce assembled particles of a modified virus; and d) harvesting assembled particles of the modified virus from said plant material.

6. The method of claim 5, in which the foreign nucleotide sequence is inserted by i) selecting two different restriction enzyme sites in the plant viral nucleic acid; ii) cutting the plant viral nucleic acid using the corresponding restriction enzymes; and iii) inserting into the cut viral nucleic acid a pair of complementary oligonucleotides which encode the foreign peptide flanked by sequences present in wild type virus which terminate in ends compatible with the restriction enzyme cutting sites.

7. A method for producing plant virus particles comprising: a) providing i) a plant virus genome comprising nucleic acid which codes for a coat protein, ii) a foreign nucleotide sequence coding for a portion of a mammalian viral protein, wherein said portion is between six and twenty-one amino acids in length; b) modifying said plant virus genome by inserting said foreign nucleotide sequence coding for a foreign peptide at a site within said nucleic acid which codes for the coat protein so as to create a modified plant virus genome comprising an insert, where assembly of the coat protein is not abolished; c) infecting plant material selected from the group consisting of plants, plant tissue, plant cells and protoplasts with said modified plant virus genome to produce assembled particles of a modified virus; and d) harvesting assembled particles of the modified virus from said plant material.

8. The method of claim 7, in which the foreign nucleotide sequence is inserted by i) selecting two different restriction enzyme sites in the plant viral nucleic acid; ii) cutting the plant viral nucleic acid using the corresponding restriction enzymes; and iii) inserting into the cut viral nucleic acid a pair of complementary oligonucleotides which encode the foreign peptide and which terminate in ends compatible with the restriction enzyme cutting sites.

9. The method of claim 7, wherein said modified plant virus genome is contained within a plasmid.

* * * * *

SEQUENCE LISTING

<160> NUMBER OF SEQ ID NOS: 123

<210> SEQ ID NO 1
<211> LENGTH: 120
<212> TYPE: DNA
<213> ORGANISM: Cowpea mosaic virus

<400> SEQUENCE: 1
ggacctgttt gtgctgaagc ctcagatgtg tatagcccat gtatgatagc tagcactcct    60
cctgctccat tttcagacgt tacagcagta acttttgact taatcaacgg caaaataact   120

<210> SEQ ID NO 2
<211> LENGTH: 40
<212> TYPE: PRT
<213> ORGANISM: Cowpea mosaic virus

<400> SEQUENCE: 2

Gly Pro Val Cys Ala Glu Ala Ser Asp Val Tyr Ser Pro Cys Met Ile
 1               5                  10                  15

Ala Ser Thr Pro Pro Ala Pro Phe Ser Asp Val Thr Ala Val Thr Phe
            20                  25                  30

Asp Leu Ile Asn Gly Lys Ile Thr
        35                  40

<210> SEQ ID NO 3
<211> LENGTH: 27
<212> TYPE: PRT
<213> ORGANISM: Foot-and-mouth disease virus

<400> SEQUENCE: 3

Ser Thr Tyr Ser Arg Asn Ala Val Pro Asn Leu Arg Gly Asp Leu Gln
 1               5                  10                  15

Val Leu Ala Gln Lys Val Ala Arg Thr Leu Pro
            20                  25

<210> SEQ ID NO 4
<211> LENGTH: 81
<212> TYPE: DNA
<213> ORGANISM: Foot-and-mouth disease virus

<400> SEQUENCE: 4
ctagcactta tagtagaaat gctgttccta atttgagagg agatcttcaa gttttggctc    60
aaaaggttgc tcggactctt c                                              81

<210> SEQ ID NO 5
<211> LENGTH: 81
<212> TYPE: DNA
<213> ORGANISM: Foot-and-mouth disease virus

<400> SEQUENCE: 5
gtgaatatca tctttacgac aaggattaaa ctctcctcta gaagttcaaa accgagtttt    60
ccaacgagcc tgagaaggat c                                              81

<210> SEQ ID NO 6
<211> LENGTH: 52
<212> TYPE: PRT
<213> ORGANISM: Foot-and-mouth disease virus

<400> SEQUENCE: 6

```
Gly Pro Val Cys Ala Glu Ala Ser Asp Val Tyr Ser Pro Cys Met Ile
 1               5                  10                  15

Ala Ser Thr Tyr Ser Arg Asn Ala Val Pro Asn Leu Arg Gly Asp Leu
            20                  25                  30

Gln Val Leu Ala Gln Lys Val Ala Arg Thr Leu Pro Ser Thr Pro Pro
         35                  40                  45

Ala Pro Phe Ser
     50

<210> SEQ ID NO 7
<211> LENGTH: 156
<212> TYPE: DNA
<213> ORGANISM: Foot-and-mouth disease virus

<400> SEQUENCE: 7
ggacctgttt gtgctgaagc ctcagatgtg tatagcccat gtatgatagc tagcacttat      60
agtagaaatg ctgttcctaa tttgagagga gatcttcaag ttttggctca aaaggttgct     120
cggactcttc ctagcactcc tcctgctcca ttttca                                156

<210> SEQ ID NO 8
<211> LENGTH: 52
<212> TYPE: PRT
<213> ORGANISM: Foot-and-mouth disease virus

<400> SEQUENCE: 8

Tyr Ser Pro Cys Met Ile Ala Ser Thr Tyr Ser Arg Asn Ala Val Pro
 1               5                  10                  15

Asn Leu Arg Gly Asp Leu Gln Val Leu Ala Gln Lys Val Ala Arg Thr
            20                  25                  30

Leu Pro Ser Thr Pro Pro Ala Pro Phe Ser Asp Val Thr Ala Val Thr
         35                  40                  45

Phe Asp Leu Ile
     50

<210> SEQ ID NO 9
<211> LENGTH: 156
<212> TYPE: DNA
<213> ORGANISM: Foot-and-mouth disease virus

<400> SEQUENCE: 9
tatagcccat gtatgatagc tagcacttat agtagaaatg ctgttcctaa tttgagagga      60
gatcttcaag ttttggctca aaaggttgct cggactcttc ctagcactcc tcctgctcca     120
ttttcagacg ttacagcagt aactttttgac ttaatc                               156

<210> SEQ ID NO 10
<211> LENGTH: 156
<212> TYPE: DNA
<213> ORGANISM: Foot-and-mouth disease virus

<400> SEQUENCE: 10
atatcgggta catactatcg atcgtgaata tcatctttac gacaaggatt aaactctcct      60
ctagaagttc aaaaccgagt tttccaacga gcctgagaag gatcgtgagg aggacgaggt     120
aaaagtctgc aatgtcgtca ttgaaaactg aattag                                156

<210> SEQ ID NO 11
<211> LENGTH: 23
<212> TYPE: PRT
<213> ORGANISM: Artificial Sequence
```

```
<220> FEATURE:
<223> OTHER INFORMATION: Description of Artificial Sequence:  Synthetic

<400> SEQUENCE: 11

Pro Cys Met Ile Ala Ser Thr Pro Pro Ala Pro Phe Ser Asp Val Thr
  1               5                  10                  15

Ala Val Thr Phe Asp Leu Ile
            20

<210> SEQ ID NO 12
<211> LENGTH: 69
<212> TYPE: DNA
<213> ORGANISM: Artificial Sequence
<220> FEATURE:
<223> OTHER INFORMATION: Description of Artificial Sequence:  Synthetic

<400> SEQUENCE: 12
ccatgtatga tagctagcac tcctcctgct ccattttcag acgttacagc agtaactttt     60
gacttaatc                                                            69

<210> SEQ ID NO 13
<211> LENGTH: 69
<212> TYPE: DNA
<213> ORGANISM: Artificial Sequence
<220> FEATURE:
<223> OTHER INFORMATION: Description of Artificial Sequence:  Synthetic

<400> SEQUENCE: 13
ccatgtatga tagctagcac tcctcctgct ccattttcag acgtcacagc agtaactttt     60
gacttaatc                                                            69

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence:  Synthetic

<400> SEQUENCE: 14

Ser Thr Asp Arg Pro Glu Gly Ile Glu Glu Glu Gly Gly Glu Arg Asp
  1               5                  10                  15

Arg Asp Arg Ser Asp
            20

<210> SEQ ID NO 15
<211> LENGTH: 67
<212> TYPE: DNA
<213> ORGANISM: Artificial Sequence
<220> FEATURE:
<223> OTHER INFORMATION: Description of Artificial Sequence:  Synthetic

<400> SEQUENCE: 15
ctagcactga ccgccctgag ggcatcgagg aagagggcgg tgagcgcgat cgtgatcgtt     60
cggacgt                                                              67

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence:  Synthetic

<400> SEQUENCE: 16
```
gtgactggcg ggactcccgt agctccttct cccgccactc gcgctagcac tagcaagcc        59

<210> SEQ ID NO 17
<211> LENGTH: 47
<212> TYPE: PRT
<213> ORGANISM: Artificial Sequence
<220> FEATURE:
<223> OTHER INFORMATION: Description of Artificial Sequence: Synthetic

<400> SEQUENCE: 17

Gly Pro Val Cys Ala Glu Ala Ser Asp Val Tyr Ser Pro Cys Met Ile
 1               5                  10                  15

Ala Ser Thr Asp Arg Pro Glu Gly Ile Glu Glu Glu Gly Gly Glu Arg
            20                  25                  30

Asp Arg Asp Arg Ser Asp Val Thr Ala Val Thr Phe Asp Leu Ile
        35                  40                  45

<210> SEQ ID NO 18
<211> LENGTH: 141
<212> TYPE: DNA
<213> ORGANISM: Artificial Sequence
<220> FEATURE:
<223> OTHER INFORMATION: Description of Artificial Sequence: Synthetic

<400> SEQUENCE: 18
ggacctgttt gtgctgaagc ctcagatgtg tatagcccat gtatgatagc tagcactgac        60
cgccctgagg gcatcgagga agagggcggt gagcgcgatc gtgatcgttc ggacgtcaca       120
gcagtaactt ttgacttaat c                                                 141

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 19

Ser Thr Pro Ala Thr Gly Ile Asp Asn His Arg Glu Ala Lys Leu Asp
 1               5                  10                  15

<210> SEQ ID NO 20
<211> LENGTH: 52
<212> TYPE: DNA
<213> ORGANISM: Artificial Sequence
<220> FEATURE:
<223> OTHER INFORMATION: Description of Artificial Sequence: Synthetic

<400> SEQUENCE: 20
ctagcactcc tgctactgga atcgataatc atagagaagc taaattggac gt                52

<210> SEQ ID NO 21
<211> LENGTH: 44
<212> TYPE: DNA
<213> ORGANISM: Artificial Sequence
<220> FEATURE:
<223> OTHER INFORMATION: Description of Artificial Sequence: Synthetic

<400> SEQUENCE: 21
gtgaggacga tgaccttagc tattagtatc tcttcgattt aacc                         44

<210> SEQ ID NO 22
<211> LENGTH: 42
<212> TYPE: PRT
<213> ORGANISM: Artificial Sequence -continued

```
<220> FEATURE:
<223> OTHER INFORMATION: Description of Artificial Sequence: Synthetic

<400> SEQUENCE: 22

Gly Pro Val Cys Ala Glu Ala Ser Asp Val Tyr Ser Pro Cys Met Ile
  1               5                  10                  15

Ala Ser Thr Pro Ala Thr Gly Ile Asp Asn His Arg Glu Ala Lys Leu
                 20                  25                  30

Asp Val Thr Ala Val Thr Phe Asp Leu Ile
             35                  40

<210> SEQ ID NO 23
<211> LENGTH: 126
<212> TYPE: DNA
<213> ORGANISM: Artificial Sequence
<220> FEATURE:
<223> OTHER INFORMATION: Description of Artificial Sequence: Synthetic

<400> SEQUENCE: 23
ggacctgttt gtgctgaagc ctcagatgtg tatagcccat gtatgatagc tagcactcct      60
gctactggaa tcgataatca tagagaagct aaattggacg tcacagcagt aacttttgac     120
ttaatc                                                                126

<210> SEQ ID NO 24
<211> LENGTH: 39
<212> TYPE: PRT
<213> ORGANISM: Foot-and-mouth disease virus

<400> SEQUENCE: 24

Tyr Ser Pro Cys Met Ile Ala Ser Thr Val Pro Asn Leu Arg Gly Asp
  1               5                  10                  15

Leu Gln Val Leu Ala Gln Lys Val Ala Arg Thr Leu Pro Asp Val Thr
                 20                  25                  30

Ala Val Thr Phe Asp Leu Ile
             35

<210> SEQ ID NO 25
<211> LENGTH: 117
<212> TYPE: DNA
<213> ORGANISM: Foot-and-mouth disease virus

<400> SEQUENCE: 25
tatagcccat gtatgatagc tagcactgtt cctaatttga gaggagatct tcaagttttg      60
gctcaaaagg ttgctcggac tcttcctgac gtcacagcag taacttttga cttaatc       117

<210> SEQ ID NO 26
<211> LENGTH: 117
<212> TYPE: DNA
<213> ORGANISM: Foot-and-mouth disease virus

<400> SEQUENCE: 26
atatcgggta catactatcg atcgtgacaa ggattaaact ctcctctaga agttcaaaac      60
cgagttttcc aacgagcctg agaaggactg cagtgtcgtc attgaaaact gaattag      117

<210> SEQ ID NO 27
<211> LENGTH: 5
<212> TYPE: PRT
<213> ORGANISM: Foot-and-mouth disease virus

<400> SEQUENCE: 27
```

```
Ser Thr Pro Pro Ala
  1               5

<210> SEQ ID NO 28
<211> LENGTH: 17
<212> TYPE: DNA
<213> ORGANISM: Foot-and-mouth disease virus

<400> SEQUENCE: 28
ctagcactcc tcctgct                                                17

<210> SEQ ID NO 29
<211> LENGTH: 13
<212> TYPE: DNA
<213> ORGANISM: Foot-and-mouth disease virus

<400> SEQUENCE: 29
gtgaggagga cga                                                    13

<210> SEQ ID NO 30
<211> LENGTH: 4
<212> TYPE: PRT
<213> ORGANISM: Foot-and-mouth disease virus

<400> SEQUENCE: 30

Pro Phe Ser Asp
  1

<210> SEQ ID NO 31
<211> LENGTH: 14
<212> TYPE: DNA
<213> ORGANISM: Foot-and-mouth disease virus

<400> SEQUENCE: 31
ccattttcag acgt                                                   14

<210> SEQ ID NO 32
<211> LENGTH: 10
<212> TYPE: DNA
<213> ORGANISM: Foot-and-mouth disease virus

<400> SEQUENCE: 32
ggtaaaagtc                                                        10

<210> SEQ ID NO 33
<211> LENGTH: 19
<212> TYPE: PRT
<213> ORGANISM: Foot-and-mouth disease virus

<400> SEQUENCE: 33

Val Pro Asn Leu Arg Gly Asp Leu Gln Val Leu Ala Gln Lys Val Ala
  1               5                  10                  15

Arg Thr Leu

<210> SEQ ID NO 34
<211> LENGTH: 57
<212> TYPE: DNA
<213> ORGANISM: Foot-and-mouth disease virus

<400> SEQUENCE: 34
gttcctaatt tgagaggaga tcttcaagtt ttggctcaaa aggttgctcg gactctt    57

<210> SEQ ID NO 35
```

-continued

```
<211> LENGTH: 57
<212> TYPE: DNA
<213> ORGANISM: Foot-and-mouth disease virus

<400> SEQUENCE: 35
caaggattaa actctcctct agaagttcaa aaccgagttt ccaacgagc ctgagaa        57

<210> SEQ ID NO 36
<211> LENGTH: 14
<212> TYPE: PRT
<213> ORGANISM: Foot-and-mouth disease virus

<400> SEQUENCE: 36

Lys Asp Ala Thr Gly Ile Asp Asn His Arg Glu Ala Lys Leu
  1               5                  10

<210> SEQ ID NO 37
<211> LENGTH: 42
<212> TYPE: DNA
<213> ORGANISM: Foot-and-mouth disease virus

<400> SEQUENCE: 37
aaagatgcta ctggaatcga taatcataga gaagcaaaat tg                       42

<210> SEQ ID NO 38
<211> LENGTH: 42
<212> TYPE: DNA
<213> ORGANISM: Foot-and-mouth disease virus

<400> SEQUENCE: 38
tttctacgat gaccttagct attagtatct cttcgtttta ac                       42

<210> SEQ ID NO 39
<211> LENGTH: 22
<212> TYPE: PRT
<213> ORGANISM: Foot-and-mouth disease virus

<400> SEQUENCE: 39

Pro Arg Gly Pro Asp Arg Pro Glu Gly Ile Glu Glu Glu Gly Gly Glu
  1               5                  10                  15

Arg Asp Arg Asp Arg Ser
            20

<210> SEQ ID NO 40
<211> LENGTH: 66
<212> TYPE: DNA
<213> ORGANISM: Foot-and-mouth disease virus

<400> SEQUENCE: 40
cctagaggac cagacagacc tgaaggaata gaagaggaag gtggagaacg cgatcgagat    60
agatca                                                              66

<210> SEQ ID NO 41
<211> LENGTH: 66
<212> TYPE: DNA
<213> ORGANISM: Foot-and-mouth disease virus

<400> SEQUENCE: 41
ggatctcctg gtctgtctgg acttccttat cttctccttc cacctcttgc gctagctcta    60
tctagt                                                              66

<210> SEQ ID NO 42
```

-continued

```
<211> LENGTH: 13
<212> TYPE: PRT
<213> ORGANISM: Soybean mosaic virus

<400> SEQUENCE: 42

Met Glu Gly Gly Ser Ser Lys Thr Ala Val Asn Thr Gly
 1               5                  10

<210> SEQ ID NO 43
<211> LENGTH: 39
<212> TYPE: DNA
<213> ORGANISM: Soybean mosaic virus

<400> SEQUENCE: 43
atggaaggag gatcatctaa gactgctgtg aacactggg                              39

<210> SEQ ID NO 44
<211> LENGTH: 39
<212> TYPE: DNA
<213> ORGANISM: Soybean mosaic virus

<400> SEQUENCE: 44
atggaaggag gatcctctaa gactgctgtg aacactggg                              39

<210> SEQ ID NO 45
<211> LENGTH: 39
<212> TYPE: DNA
<213> ORGANISM: Soybean mosaic virus

<400> SEQUENCE: 45
atggaaggag gatcatctaa gactgctgtt aacactggg                              39

<210> SEQ ID NO 46
<211> LENGTH: 16
<212> TYPE: PRT
<213> ORGANISM: Homo sapiens

<400> SEQUENCE: 46

Gly Val Thr Ser Ala Pro Asp Thr Arg Pro Ala Pro Gly Ser Thr Ala
 1               5                  10                  15

<210> SEQ ID NO 47
<211> LENGTH: 48
<212> TYPE: DNA
<213> ORGANISM: Homo sapiens

<400> SEQUENCE: 47
ggtgttactt ctgctcctga tactagacct gctcctggtt ctactgct                    48

<210> SEQ ID NO 48
<211> LENGTH: 48
<212> TYPE: DNA
<213> ORGANISM: Homo sapiens

<400> SEQUENCE: 48
ccacaatgaa gacgaccact atgatctgga cgaggaccaa gatgacga                    48

<210> SEQ ID NO 49
<211> LENGTH: 68
<212> TYPE: DNA
<213> ORGANISM: Artificial Sequence
<220> FEATURE:
<223> OTHER INFORMATION: Description of Artificial Sequence: Synthetic

<400> SEQUENCE: 49
```

```
gatccggtgt tacttctgct cctgatacta gacctgctcc tggttctact gcttctaaga      60
ctgctgtt                                                               68

<210> SEQ ID NO 50
<211> LENGTH: 64
<212> TYPE: DNA
<213> ORGANISM: Artificial Sequence
<220> FEATURE:
<223> OTHER INFORMATION: Description of Artificial Sequence:  Synthetic

<400> SEQUENCE: 50
gccacaatga agacgaccac tatgatctgg acgaggacca agatgacgaa gattctgacg      60
acaa                                                                   64

<210> SEQ ID NO 51
<211> LENGTH: 68
<212> TYPE: DNA
<213> ORGANISM: Artificial Sequence
<220> FEATURE:
<223> OTHER INFORMATION: Description of Artificial Sequence:  Synthetic

<400> SEQUENCE: 51
gatcctctgg tgttacttct gctcctgata ctagacctgc tcctggttct actgctaaga      60
ctgctgtt                                                               68

<210> SEQ ID NO 52
<211> LENGTH: 64
<212> TYPE: DNA
<213> ORGANISM: Artificial Sequence
<220> FEATURE:
<223> OTHER INFORMATION: Description of Artificial Sequence:  Synthetic

<400> SEQUENCE: 52
gagaccacaa tgaagacgac cactatgatc tggacgagga ccaagatgac gattctgacg      60
acaa                                                                   64

<210> SEQ ID NO 53
<211> LENGTH: 68
<212> TYPE: DNA
<213> ORGANISM: Artificial Sequence
<220> FEATURE:
<223> OTHER INFORMATION: Description of Artificial Sequence:  Synthetic

<400> SEQUENCE: 53
gatcctctaa gggtgttact tctgctcctg atactagacc tgctcctggt tctactgcta      60
ctgctgtt                                                               68

<210> SEQ ID NO 54
<211> LENGTH: 64
<212> TYPE: DNA
<213> ORGANISM: Artificial Sequence
<220> FEATURE:
<223> OTHER INFORMATION: Description of Artificial Sequence:  Synthetic

<400> SEQUENCE: 54
gagattccca caatgaagac gaccactatg atctggacga ggaccaagat gacgatgacg      60
acaa                                                                   64

<210> SEQ ID NO 55
<211> LENGTH: 68
<212> TYPE: DNA
```

-continued

<213> ORGANISM: Artificial Sequence
<220> FEATURE:
<223> OTHER INFORMATION: Description of Artificial Sequence: Synthetic

<400> SEQUENCE: 55
gatcctctaa gactggtgtt acttctgctc ctgatactag acctgctcct ggttctactg 60
ctgctgtt 68

<210> SEQ ID NO 56
<211> LENGTH: 64
<212> TYPE: DNA
<213> ORGANISM: Artificial Sequence
<220> FEATURE:
<223> OTHER INFORMATION: Description of Artificial Sequence: Synthetic

<400> SEQUENCE: 56
gagattctga ccacaatgaa gacgaccact atgatctgga cgaggaccaa gatgacgacg 60
acaa 64

<210> SEQ ID NO 57
<211> LENGTH: 68
<212> TYPE: DNA
<213> ORGANISM: Artificial Sequence
<220> FEATURE:
<223> OTHER INFORMATION: Description of Artificial Sequence: Synthetic

<400> SEQUENCE: 57
gatcctctaa gactgctggt gttacttctg ctcctgatac tagacctgct cctggttcta 60
ctgctgtt 68

<210> SEQ ID NO 58
<211> LENGTH: 64
<212> TYPE: DNA
<213> ORGANISM: Artificial Sequence
<220> FEATURE:
<223> OTHER INFORMATION: Description of Artificial Sequence: Synthetic

<400> SEQUENCE: 58
gagattctga cgaccacaat gaagacgacc actatgatct ggacgaggac caagatgacg 60
acaa 64

<210> SEQ ID NO 59
<211> LENGTH: 33
<212> TYPE: PRT
<213> ORGANISM: Soybean mosaic virus

<400> SEQUENCE: 59

Asn Ile Tyr Ala Pro Ala Arg Leu Thr Ile Ala Ala Ala Asn Ser Ser
1 5 10 15

Ile Asn Ile Ala Ser Val Gly Thr Leu Tyr Ala Thr Tyr Glu Val Glu
20 25 30

Leu

<210> SEQ ID NO 60
<211> LENGTH: 37
<212> TYPE: PRT
<213> ORGANISM: Soybean mosaic virus

<400> SEQUENCE: 60

Asn Ile Gly Asn Ile Leu Val Pro Ala Arg Leu Val Ile Ala Met Glu
1 5 10 15

```
Gly Gly Ser Ser Lys Thr Ala Val Asn Thr Gly Arg Leu Tyr Ala Ser
            20                  25                  30

Tyr Thr Ile Arg Leu
        35

<210> SEQ ID NO 61
<211> LENGTH: 37
<212> TYPE: PRT
<213> ORGANISM: Soybean mosaic virus

<400> SEQUENCE: 61

Asn Ile Ala Thr Asp Leu Val Pro Ala Arg Leu Val Ile Ala Leu Leu
 1               5                  10                  15

Asp Gly Ser Ser Ser Thr Ala Val Ala Ala Gly Arg Ile Tyr Ala Ser
            20                  25                  30

Tyr Thr Ile Gln Met
        35

<210> SEQ ID NO 62
<211> LENGTH: 17
<212> TYPE: PRT
<213> ORGANISM: Lucerne transient streak virus

<400> SEQUENCE: 62

Ile Ala Ala Ala Asn Ser Ser Ile Asn Ile Ala Ser Val Gly Thr Leu
 1               5                  10                  15

Tyr

<210> SEQ ID NO 63
<211> LENGTH: 51
<212> TYPE: DNA
<213> ORGANISM: Lucerne transient streak virus

<400> SEQUENCE: 63
atagccgcag ctaacagctc cataaacata gctagtgtgg gtactcttta t          51

<210> SEQ ID NO 64
<211> LENGTH: 51
<212> TYPE: DNA
<213> ORGANISM: Lucerne transient streak virus

<400> SEQUENCE: 64
atagctgcag ctaacagctc cataaacata gctagtgtgg gtactcttta t          51

<210> SEQ ID NO 65
<211> LENGTH: 51
<212> TYPE: DNA
<213> ORGANISM: Lucerne transient streak virus

<400> SEQUENCE: 65
atagccgcag ctaacagctc cataaacata gctagtgtgg gtacccttta t          51

<210> SEQ ID NO 66
<211> LENGTH: 16
<212> TYPE: PRT
<213> ORGANISM: Homo sapiens

<400> SEQUENCE: 66

Gly Val Thr Ser Ala Pro Asp Thr Arg Pro Ala Pro Gly Ser Thr Ala
 1               5                  10                  15

<210> SEQ ID NO 67
```

-continued

```
<211> LENGTH: 48
<212> TYPE: DNA
<213> ORGANISM: Homo sapiens

<400> SEQUENCE: 67
ggtgttactt ctgctcctga tactagacct gctcctggtt ctactgct                    48

<210> SEQ ID NO 68
<211> LENGTH: 48
<212> TYPE: DNA
<213> ORGANISM: Homo sapiens

<400> SEQUENCE: 68
ccacaatgaa gacgaccact atgatctgga cgaggaccaa gatgacga                    48

<210> SEQ ID NO 69
<211> LENGTH: 83
<212> TYPE: DNA
<213> ORGANISM: Lucerne transient streak virus

<400> SEQUENCE: 69
gctaacagcg gtgttacttc tgctcctgat actagacctg ctcctggttc tactgcttcc       60
ataaacatag ctagtgtggg tac                                               83

<210> SEQ ID NO 70
<211> LENGTH: 83
<212> TYPE: DNA
<213> ORGANISM: Lucerne transient streak virus

<400> SEQUENCE: 70
acgtcgattg tcgccacaat gaagacgacc actatgatct ggacgaggac caagatgacg       60
aaggtatttg tatcgatcac acc                                               83

<210> SEQ ID NO 71
<211> LENGTH: 83
<212> TYPE: DNA
<213> ORGANISM: Lucerne transient streak virus

<400> SEQUENCE: 71
gctaacagct ccggtgttac ttctgctcct gatactagac ctgctcctgg ttctactgct       60
ataaacatag ctagtgtggg tac                                               83

<210> SEQ ID NO 72
<211> LENGTH: 83
<212> TYPE: DNA
<213> ORGANISM: Lucerne transient streak virus

<400> SEQUENCE: 72
acgtcgattg tcgaggccac aatgaagacg accactatga tctggacgag gaccaagatg       60
acgatatttg tatcgatcac acc                                               83

<210> SEQ ID NO 73
<211> LENGTH: 83
<212> TYPE: DNA
<213> ORGANISM: Lucerne transient streak virus

<400> SEQUENCE: 73
gctaacagct ccataggtgt tacttctgct cctgatacta gacctgctcc tggttctact       60
gctaacatag ctagtgtggg tac                                               83
```

<210> SEQ ID NO 74
<211> LENGTH: 83
<212> TYPE: DNA
<213> ORGANISM: Lucerne transient streak virus

<400> SEQUENCE: 74
acgtcgattg tcgaggtatc cacaatgaag acgaccacta tgatctggac gaggaccaag    60
atgacgattg tatcgatcac acc                                            83

<210> SEQ ID NO 75
<211> LENGTH: 83
<212> TYPE: DNA
<213> ORGANISM: Lucerne transient streak virus

<400> SEQUENCE: 75
gctaacagct ccataaacgg tgttacttct gctcctgata ctagacctgc tcctggttct    60
actgctatag ctagtgtggg tac                                            83

<210> SEQ ID NO 76
<211> LENGTH: 83
<212> TYPE: DNA
<213> ORGANISM: Lucerne transient streak virus

<400> SEQUENCE: 76
acgtcgattg tcgaggtatt tgccacaatg aagacgacca ctatgatctg gacgaggacc    60
aagatgacga tatcgatcac acc                                            83

<210> SEQ ID NO 77
<211> LENGTH: 83
<212> TYPE: DNA
<213> ORGANISM: Lucerne transient streak virus

<400> SEQUENCE: 77
gctaacagct ccataaacat aggtgttact tctgctcctg atactagacc tgctcctggt    60
tctactgctg ctagtgtggg tac                                            83

<210> SEQ ID NO 78
<211> LENGTH: 83
<212> TYPE: DNA
<213> ORGANISM: Lucerne transient streak virus

<400> SEQUENCE: 78
acgtcgattg tcgaggtatt tgtatccaca atgaagacga ccactatgat ctggacgagg    60
accaagatga cgacgatcac acc                                            83

<210> SEQ ID NO 79
<211> LENGTH: 83
<212> TYPE: DNA
<213> ORGANISM: Lucerne transient streak virus

<400> SEQUENCE: 79
gctaacagct ccataaacat agctggtgtt acttctgctc ctgatactag acctgctcct    60
ggttctactg ctagtgtggg tac                                            83

<210> SEQ ID NO 80
<211> LENGTH: 83
<212> TYPE: DNA
<213> ORGANISM: Lucerne transient streak virus

<400> SEQUENCE: 80

```
acgtcgattg tcgaggtatt tgtatcgacc acaatgaaga cgaccactat gatctggacg    60
aggaccaaga tgacgatcac acc                                           83
```

<210> SEQ ID NO 81
<211> LENGTH: 324
<212> TYPE: PRT
<213> ORGANISM: Tomato bushy stunt virus

<400> SEQUENCE: 81

```
Lys Lys Gln Gln Met Ile Asn His Val Gly Gly Thr Gly Gly Ala Ile
  1               5                  10                  15

Met Ala Pro Val Ala Val Thr Arg Gln Leu Val Gly Ser Lys Pro Lys
             20                  25                  30

Phe Thr Gly Arg Thr Ser Gly Ser Val Thr Val Thr His Arg Glu Tyr
         35                  40                  45

Leu Ser Gln Val Asn Asn Ser Thr Gly Phe Gln Val Asn Gly Gly Ile
     50                  55                  60

Val Gly Asn Leu Leu Gln Leu Asn Pro Leu Asn Gly Thr Leu Phe Ser
 65                  70                  75                  80

Trp Leu Pro Ala Ile Ala Ser Asn Phe Asp Gln Tyr Thr Phe Asn Ser
                 85                  90                  95

Val Val Leu His Tyr Val Pro Leu Cys Ser Thr Thr Glu Val Gly Arg
            100                 105                 110

Val Ala Ile Tyr Phe Asp Lys Asp Ser Glu Asp Pro Glu Pro Ala Asp
        115                 120                 125

Arg Val Glu Leu Ala Asn Tyr Ser Val Leu Lys Glu Thr Ala Pro Trp
    130                 135                 140

Ala Glu Ala Met Leu Arg Val Pro Thr Asp Lys Ile Lys Arg Phe Cys
145                 150                 155                 160

Asp Asp Ser Ser Thr Ser Asp His Lys Leu Ile Asp Leu Gly Gln Leu
                165                 170                 175

Gly Ile Ala Thr Tyr Gly Gly Ala Gly Thr Asn Ala Val Gly Asp Ile
            180                 185                 190

Phe Ile Ser Tyr Ser Val Thr Leu Tyr Phe Pro Gln Pro Thr Asn Thr
        195                 200                 205

Leu Leu Ser Thr Arg Arg Leu Asp Leu Ala Gly Ala Leu Val Thr Ala
    210                 215                 220

Ser Gly Pro Gly Tyr Leu Leu Val Ser Arg Thr Ala Thr Val Leu Thr
225                 230                 235                 240

Met Thr Phe Arg Ala Thr Gly Thr Phe Val Ile Ser Gly Thr Tyr Arg
                245                 250                 255

Cys Leu Thr Ala Thr Thr Leu Gly Leu Ala Gly Gly Val Asn Val Asn
            260                 265                 270

Ser Ile Thr Val Val Asp Asn Ile Gly Thr Asp Ser Ala Phe Phe Ile
        275                 280                 285

Asn Cys Thr Val Ser Asn Leu Pro Ser Val Val Thr Phe Thr Ser Thr
    290                 295                 300

Gly Ile Thr Ser Ala Thr Val His Cys Val Arg Ala Thr Arg Gln Asn
305                 310                 315                 320

Asp Val Ser Leu
```

<210> SEQ ID NO 82
<211> LENGTH: 331
<212> TYPE: PRT
<213> ORGANISM: Red clover necrotic mosaic virus -continued

<400> SEQUENCE: 82

```
Lys Ser Lys Gln Arg Ser Gln Pro Arg Asn Arg Thr Pro Asn Thr Ser
  1               5                  10                  15

Val Lys Thr Val Ala Ile Pro Phe Ala Lys Thr Gln Ile Ile Lys Thr
             20                  25                  30

Val Asn Pro Pro Pro Lys Pro Ala Arg Gly Ile Leu His Thr Gln Leu
         35                  40                  45

Val Met Ser Val Val Gly Ser Val Gln Met Arg Thr Asn Asn Gly Lys
     50                  55                  60

Ser Asn Gln Arg Phe Arg Leu Asn Pro Ser Asn Pro Ala Leu Phe Pro
 65                  70                  75                  80

Thr Leu Ala Tyr Glu Ala Ala Asn Tyr Asp Met Tyr Arg Leu Lys Lys
                 85                  90                  95

Leu Thr Leu Arg Tyr Val Pro Leu Val Thr Val Gln Asn Ser Gly Arg
            100                 105                 110

Val Ala Met Ile Trp Asp Pro Asp Ser Gln Asp Ser Ala Pro Gln Ser
        115                 120                 125

Arg Gln Glu Ile Ser Ala Tyr Ser Arg Ser Val Ser Thr Ala Val Tyr
    130                 135                 140

Glu Lys Cys Ser Leu Thr Ile Pro Ala Asp Asn Gln Trp Arg Phe Val
145                 150                 155                 160

Ala Asp Asn Thr Thr Val Asp Arg Lys Leu Val Asp Phe Gly Gln Leu
                165                 170                 175

Leu Phe Val Thr His Ser Gly Ser Asp Gly Ile Glu Thr Gly Asp Ile
            180                 185                 190

Phe Leu Asp Cys Glu Val Glu Phe Lys Gly Pro Gln Pro Thr Ala Ser
        195                 200                 205

Ile Val Gln Lys Thr Val Ile Asp Leu Gly Gly Thr Leu Thr Ser Phe
    210                 215                 220

Glu Gly Pro Ser Tyr Leu Met Pro Pro Asp Ala Phe Ile Thr Ser Ser
225                 230                 235                 240

Ser Phe Gly Leu Phe Val Asp Val Ala Gly Thr Tyr Leu Leu Thr Leu
                245                 250                 255

Val Val Thr Cys Ser Thr Thr Gly Ser Val Thr Val Gly Gly Asn Ser
            260                 265                 270

Thr Leu Val Gly Asp Gly Arg Ala Ala Tyr Gly Ser Ser Asn Tyr Ile
        275                 280                 285

Ala Ser Ile Val Phe Thr Ser Ser Gly Val Leu Ser Thr Thr Pro Ser
    290                 295                 300

Val Gln Phe Ser Gly Ser Ser Gly Val Ser Arg Val Gln Met Asn Ile
305                 310                 315                 320

Cys Arg Cys Lys Gln Gly Asn Thr Phe Ile Leu
                325                 330
```

<210> SEQ ID NO 83
<211> LENGTH: 41
<212> TYPE: PRT
<213> ORGANISM: Red clover necrotic mosaic virus

<400> SEQUENCE: 83

```
Ala Ser Ile Val Gln Lys Thr Val Ile Asp Leu Gly Gly Thr Leu Thr
  1               5                  10                  15

Ser Phe Glu Gly Pro Ser Tyr Leu Met Pro Pro Asp Ala Phe Ile Thr
             20                  25                  30

-continued

```
Ser Ser Ser Phe Gly Leu Phe Val Asp
        35                  40

<210> SEQ ID NO 84
<211> LENGTH: 27
<212> TYPE: PRT
<213> ORGANISM: Red clover necrotic mosaic virus

<400> SEQUENCE: 84

Ala Ser Ile Val Gln Lys Tyr Val Ile Asp Leu Gly Gly Thr Leu Thr
1               5                   10                  15

Ser Phe Glu Gly Pro Ser Tyr Leu Met Pro Pro
            20                  25

<210> SEQ ID NO 85
<211> LENGTH: 17
<212> TYPE: PRT
<213> ORGANISM: Red clover necrotic mosaic virus

<400> SEQUENCE: 85

Ser Ile Val Gln Lys Thr Val Ile Asp Leu Gly Gly Thr Leu Thr Ser
1               5                   10                  15

Phe

<210> SEQ ID NO 86
<211> LENGTH: 51
<212> TYPE: DNA
<213> ORGANISM: Red clover necrotic mosaic virus

<400> SEQUENCE: 86
agcatcgtac agaaaactgt aattgatctc ggtgggacac tcacttcttt c          51

<210> SEQ ID NO 87
<211> LENGTH: 51
<212> TYPE: DNA
<213> ORGANISM: Red clover necrotic mosaic virus

<400> SEQUENCE: 87
agcatcgtgc acaaaactgt aattgatctc ggtgggacac tcacttcttt c          51

<210> SEQ ID NO 88
<211> LENGTH: 51
<212> TYPE: DNA
<213> ORGANISM: Red clover necrotic mosaic virus

<400> SEQUENCE: 88
agcatcgtac agaaaactgt aattgatctc ggtgggacgt taacttcttt c          51

<210> SEQ ID NO 89
<211> LENGTH: 16
<212> TYPE: PRT
<213> ORGANISM: Homo sapiens

<400> SEQUENCE: 89

Gly Val Thr Ser Ala Pro Asp Thr Arg Pro Ala Pro Gly Ser Thr Ala
1               5                   10                  15

<210> SEQ ID NO 90
<211> LENGTH: 48
<212> TYPE: DNA
<213> ORGANISM: Homo sapiens

<400> SEQUENCE: 90
```

```
ggtgttactt ctgctcctga tactagacct gctcctggtt ctactgct                48
```

<210> SEQ ID NO 91
<211> LENGTH: 48
<212> TYPE: DNA
<213> ORGANISM: Homo sapiens

<400> SEQUENCE: 91

```
ccacaatgaa gacgaccact atgatctgga cgaggaccaa gatgacga                48
```

<210> SEQ ID NO 92
<211> LENGTH: 78
<212> TYPE: DNA
<213> ORGANISM: Red clover necrotic mosaic virus

<400> SEQUENCE: 92

```
gaaaactgta ggtgttactt ctgctcctga tactagacct gctcctggtt ctactgctat   60
tgatctcggt gggacgtt                                                 78
```

<210> SEQ ID NO 93
<211> LENGTH: 82
<212> TYPE: DNA
<213> ORGANISM: Red clover necrotic mosaic virus

<400> SEQUENCE: 93

```
acgtcttttg acatccacaa tgaagacgac cactatgatc tggacgagga ccaagatgac   60
gataactaga gccaccctgc aa                                            82
```

<210> SEQ ID NO 94
<211> LENGTH: 78
<212> TYPE: DNA
<213> ORGANISM: Red clover necrotic mosaic virus

<400> SEQUENCE: 94

```
gaaaactgta attggtgtta cttctgctcc tgatactaga cctgctcctg gttctactgc   60
tgatctcggt gggacgtt                                                 78
```

<210> SEQ ID NO 95
<211> LENGTH: 82
<212> TYPE: DNA
<213> ORGANISM: Red clover necrotic mosaic virus

<400> SEQUENCE: 95

```
acgtcttttg acattaacca caatgaagac gaccactatg atctggacga ggaccaagat   60
gacgactaga gccaccctgc aa                                            82
```

<210> SEQ ID NO 96
<211> LENGTH: 78
<212> TYPE: DNA
<213> ORGANISM: Red clover necrotic mosaic virus

<400> SEQUENCE: 96

```
gaaaactgta attgatggtg ttacttctgc tcctgatact agacctgctc ctggttctac   60
tgctctcggt gggacgtt                                                 78
```

<210> SEQ ID NO 97
<211> LENGTH: 82
<212> TYPE: DNA
<213> ORGANISM: Red clover necrotic mosaic virus

```
<400> SEQUENCE: 97
acgtcttttg acattaacta ccacaatgaa gacgaccact atgatctgga cgaggaccaa    60
gatgacgaga gccaccctgc aa                                             82

<210> SEQ ID NO 98
<211> LENGTH: 78
<212> TYPE: DNA
<213> ORGANISM: Red clover necrotic mosaic virus

<400> SEQUENCE: 98
gaaaactgta attgatctcg gtgttacttc tgctcctgat actagacctg ctcctggttc    60
tactgctggt gggacgtt                                                  78

<210> SEQ ID NO 99
<211> LENGTH: 82
<212> TYPE: DNA
<213> ORGANISM: Red clover necrotic mosaic virus

<400> SEQUENCE: 99
acgtcttttg acattaacta gagccacaat gaagacgacc actatgatct ggacgaggac    60
caagatgacg accaccctgc aa                                             82

<210> SEQ ID NO 100
<211> LENGTH: 78
<212> TYPE: DNA
<213> ORGANISM: Red clover necrotic mosaic virus

<400> SEQUENCE: 100
gaaaactgta attgatctcg gtggtgttac ttctgctcct gatactagac ctgctcctgg    60
ttctactgct gggacgtt                                                  78

<210> SEQ ID NO 101
<211> LENGTH: 82
<212> TYPE: DNA
<213> ORGANISM: Red clover necrotic mosaic virus

<400> SEQUENCE: 101
acgtcttttg acattaacta gagccaccac aatgaagacg accactatga tctggacgag    60
gaccaagatg acgaccctgc aa                                             82

<210> SEQ ID NO 102
<211> LENGTH: 78
<212> TYPE: DNA
<213> ORGANISM: Red clover necrotic mosaic virus

<400> SEQUENCE: 102
gaaaactgta attgatctcg gtgggggtgt tacttctgct cctgatacta gacctgctcc    60
tggttctact gctacgtt                                                  78

<210> SEQ ID NO 103
<211> LENGTH: 82
<212> TYPE: DNA
<213> ORGANISM: Red clover necrotic mosaic virus

<400> SEQUENCE: 103
acgtcttttg acattaacta gagccacccc cacaatgaag acgaccacta tgatctggac    60
gaggaccaag atgacgatgc aa                                             82
```

```
<210> SEQ ID NO 104
<211> LENGTH: 24
<212> TYPE: PRT
<213> ORGANISM: Tobacco rattle virus

<400> SEQUENCE: 104

Ser Thr P

-continued

```
<400> SEQUENCE: 110
tcgactccgg cctcgggggg aagtggtgca acaccacctc cttgatgtcg tcaaatcaaa      60
cctttaagg                                                              69

<210> SEQ ID NO 111
<211> LENGTH: 68
<212> TYPE: DNA
<213> ORGANISM: Tobacco rattle virus

<400> SEQUENCE: 111
gaggccggag ccccccttca ccacgttgtg gtggaggaac tacagcagtt tagtttggaa      60
attccctg                                                               68

<210> SEQ ID NO 112
<211> LENGTH: 9
<212> TYPE: PRT
<213> ORGANISM: Tobacco rattle virus

<400> SEQUENCE: 112

Ser Thr Pro Ala Ser Gly Gly Ser Gly
  1               5

<210> SEQ ID NO 113
<211> LENGTH: 54
<212> TYPE: DNA
<213> ORGANISM: Tobacco rattle virus

<400> SEQUENCE: 113
tcgactccgg cctcgggggg aagtggttga tgtcgtcaaa tcaaacctttt aagg           54

<210> SEQ ID NO 114
<211> LENGTH: 53
<212> TYPE: DNA
<213> ORGANISM: Tobacco rattle virus

<400> SEQUENCE: 114
gaggccggag ccccccttca ccaactacag cagtttagtt tggaaattcc ctg             53

<210> SEQ ID NO 115
<211> LENGTH: 4
<212> TYPE: PRT
<213> ORGANISM: Tobacco rattle virus

<400> SEQUENCE: 115

Ser Thr Pro Ala
  1

<210> SEQ ID NO 116
<211> LENGTH: 39
<212> TYPE: DNA
<213> ORGANISM: Tobacco rattle virus

<400> SEQUENCE: 116
tcgactccgg cctgatgtcg tcaaatcaaa cctttaagg                             39

<210> SEQ ID NO 117
<211> LENGTH: 38
<212> TYPE: DNA
<213> ORGANISM: Tobacco rattle virus

<400> SEQUENCE: 117
gaggccggac tacagcagtt tagtttggaa attccctg                              38
```

```
<210> SEQ ID NO 118
<211> LENGTH: 2
<212> TYPE: PRT
<213> ORGANISM: Tobacco rattle virus

<400> SEQUENCE: 118

Ser Thr
  1

<210> SEQ ID NO 119
<211> LENGTH: 33
<212> TYPE: DNA
<213> ORGANISM: Tobacco rattle virus

<400> SEQUENCE: 119
tcgacttgat gtcgtcaaat caaacctta agg                              33

<210> SEQ ID NO 120
<211> LENGTH: 32
<212> TYPE: DNA
<213> ORGANISM: Tobacco rattle virus

<400> SEQUENCE: 120
gaactacagc agtttagttt ggaaattccc tg                              32

<210> SEQ ID NO 121
<211> LENGTH: 31
<212> TYPE: PRT
<213> ORGANISM: S. aureus

<400> SEQUENCE: 121

Gly Gln Asn Asn Gly Asn Gln Ser Phe Glu Glu Asp Thr Glu Lys Asp
  1               5                  10                  15

Lys Pro Lys Tyr Glu Gln Gly Gly Asn Ile Ile Asp Ile Asp Phe
             20                  25                  30

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 122
ctagcatgaa ttttgaccctt c                                         21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 123
gtacttaaaa ctggaagaat t                                          21
```